(12) United States Patent
Schulz et al.

(10) Patent No.: US 6,683,297 B2
(45) Date of Patent: Jan. 27, 2004

(54) FIBER GRATING MOISTURE AND CHEMICAL SENSING SYSTEM

(76) Inventors: Whitten Lee Schulz, 22136 NE. Chinook Way, Fairview, OR (US) 97024; Eric Udd, 2555 NE. 205th, Fairview, OR (US) 97024

(*) Notice: Subject to any disclaimer, the term of this patent is extended or adjusted under 35 U.S.C. 154(b) by 0 days.

(21) Appl. No.: 10/457,845

(22) Filed: Jun. 10, 2003

(65) Prior Publication Data

US 2003/0201385 A1 Oct. 30, 2003

Related U.S. Application Data

(62) Division of application No. 09/746,037, filed on Dec. 22, 2000, now Pat. No. 6,600,149.
(60) Provisional application No. 60/173,359, filed on Dec. 27, 1999.

(51) Int. Cl.[7] .............................. G01J 1/04; G01J 4/00
(52) U.S. Cl. ........................ 250/227.16; 250/227.17; 385/12
(58) Field of Search .................. 250/227.14, 227.15, 250/227.16, 227.17, 227.18, 227.21; 385/10, 12, 13; 73/800

(56) References Cited

U.S. PATENT DOCUMENTS

| | | | | |
|---|---|---|---|---|
| 5,378,889 A | * | 1/1995 | Lawrence | 250/227.16 |
| 5,399,854 A | * | 3/1995 | Dunphy et al. | 250/227.17 |
| 5,744,794 A | * | 4/1998 | Michie et al. | 250/227.16 |
| 5,774,619 A | * | 6/1998 | Bruesselbach | 385/137 |
| 5,945,665 A | | 8/1999 | Hay | |
| 6,218,661 B1 | | 4/2001 | Schroeder et al. | |

OTHER PUBLICATIONS

Schulz et al, "Advanced Fiber Grating Strain Sensor Systems For Bridges, Structures, and Highways" SPIE Proceedings, vol. 3325 p. 212, 1998.
Seim, et al, "Composite Strengthening and Instrumentation of the Horsetail Falls Bridge with Long Guage Length Fiber Grating Strain Sensors" SPIE Proceedings vol. 3746, p. 196, 1999.
Schulz et al, "Health Monitoring of an Adhesive Joint Using a Multi–Axis Fiber Grating Strain Sensor System" SPIE Proceedings vol. 3586, p. 41, 1999.
Schulz et al, "Progress on Monitoring of Adhesive Joints Using Multi Axis Fiber Grating Sensors." SPIE Proceedings, vol. 3991 p. 52, 2000.

* cited by examiner

Primary Examiner—Huy Mai

(57) ABSTRACT

Fiber grating environmental measurement systems are comprised of sensors that are configured to respond to changes in moisture or chemical content of the surrounding medium through the action of coatings and plates inducing strain that is measured. These sensors can also be used to monitor the interior of bonds for degradation due to aging, cracking, or chemical attack. Means to multiplex these sensors at high speed and with high sensitivity can be accomplished by using spectral filters placed to correspond to each fiber grating environmental sensor. By forming networks of spectral elements and using wavelength division multiplexing arrays of fiber grating sensors may be processed in a single fiber line allowing distributed high sensitivity, high bandwidth fiber optic grating environmental sensor systems to be realized.

15 Claims, 55 Drawing Sheets

Permeable
601

Holed
603

Slotted
605

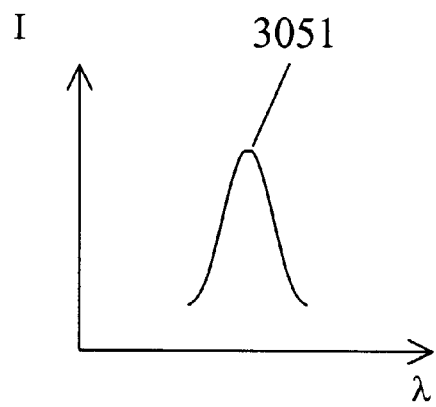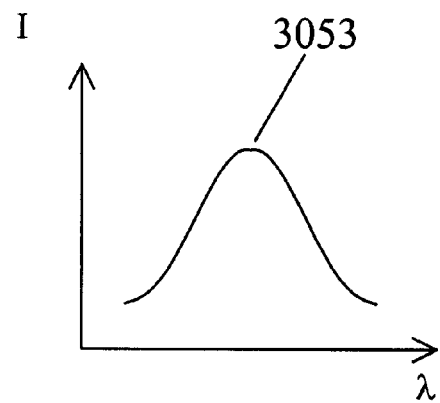
Narrower FWHM
Figure 28a
Wider FWHM
Figure 28b

Reflected Peak at Lower
Center Wavelength

Reflected Peak at Higher
Center Wavelength

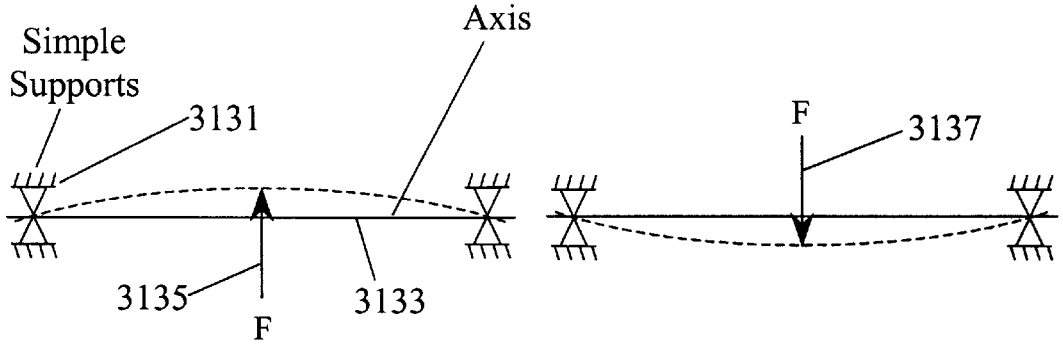
Figure 30a — Force (F) Bending Beam Up and Inducing Tension in Grating
Figure 30b — Force (F) Bending Beam Down and Inducing Compression in Grating Cantilever Beam with Grating
Attached to Top or Embedded
Above Neutral Axis Force (F) Bending
Beam Up and Inducing
Tension in Grating Force (F) Bending Beam
Down and Inducing
Compression in Grating

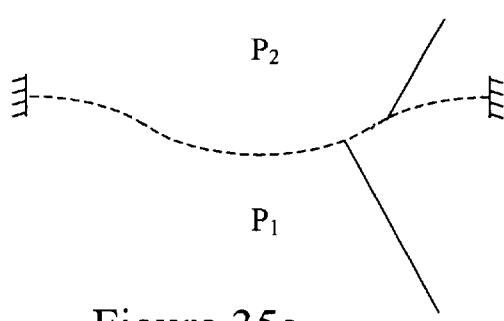
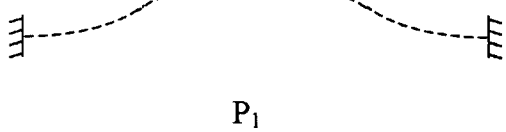
Figure 35a
Figure 35b
Diaphragm with surface mounted or embedded fiber grating

3247

FIBER GRATING MOISTURE AND CHEMICAL SENSING SYSTEM

REFERENCE TO RELATED PATENTS

This disclosure describes means to enhance the speed and sensitivity of fiber grating sensors systems to measure environmental effects and means to multiplex these sensors while retaining high speed characteristics. The background of these types of fiber grating sensors may be found in U.S. Pat. Nos. 5,380,995, 5,402,231, 5,592,965, 5,841,131 and 6,144,026. The teachings in those patents are incorporated into this disclosure by reference as though fully set forth below.

This application is a divisional of patent Ser. No. 09/746,037, granted Dec. 22, 2000 now U.S. Pat. No. 6,600,149. This application claims the benefit of U.S. Provisional Application No. 60/173,359 by Whitten L. Schulz, John Seim and Eric Udd, entitled, "Fiber Grating Environmental Sensing System" which was filed on Dec. 27, 1999. This invention was made with Government support from contract DE-FG03-99ER82753 awarded by DOE and by contracts N68335-98-C-0122 and N68335-99-C-0242 awarded by NAVAIR. The government has certain rights to this invention.

BACKGROUND OF THE INVENTION

This invention relates generally to fiber optic grating systems and more particularly, to the measurement of environmental effects using fiber optic grating sensors. Typical fiber optic grating sensor systems are described in detail in U.S. Pat. Nos. 5,380,995, 5,402,231, 5,592,965, 5,841,131 and 6,144,026.

The need for low cost, a high performance fiber optic grating environmental sensor system that is capable of long term environmental monitoring, virtually immune to electromagnetic interference and passive is critical for such applications as moisture sensing and monitoring of adhesive bonds: Another advantage of these system is that when they are appropriately configured the frequency response of the system can be very high.

The present invention includes multi-axis fiber grating sensors that may be used to sense axial strain and temperature, or axial and transverse strain simultaneously to detect chemical changes such as moisture by using appropriate transducers or changes to the structural integrity of coatings such as adhesive bonds. Means are also described to multiplex these fiber grating sensors allowing high sensitivity and high speed measurements to be made.

In U.S. Pat. Nos. 5,380,995 and 5,397,891 fiber grating demodulation systems are described that involve single element fiber gratings and using spectral filters to demodulate fiber gratings. The present invention includes means to extend the demodulation system to multiple fiber grating sensors operating at high speed on a single fiber line. In U.S. Pat. Nos. 5,591,965, 5,627,927 the usage of fiber gratings to detect more than one dimension of strain is described. These ideas are extended in U.S. Pat. Nos. 5,869,835, 5,828,059 and 5,841,131 to include fibers with different geometries that can be used to enhance sensitivity or simplify alignment procedures for enhanced sensitivity of multi-parameter fiber sensing. In U.S. patent application Ser. No. 09/176,515, "High Speed Demodulation Systems for Fiber Grating Sensors", by Eric Udd and Andreas Weisshaar means are described to process the output from multi-axis fiber grating sensors for improved sensitivity. All of these patents teaching are background for the present invention which optimizes the fiber grating sensor for optimum response to strain changes induced by changes in the state of its coating or surrounding media to form water/chemical sensors and monitor the status of adhesive joints through measurements of strain interior to the bond.

The present invention consists of an optical fiber whose axial, transverse and or temperature sensitivity has been optimized through the construction of the optical fiber or mechanical mechanisms to enhance sensitivity. High speed demodulation is provided by wavelength division multiplexing of these fiber grating sensors using series of fiber grating filters. The spectral filters are arranged so that each fiber grating sensor has a corresponding filter to match it, allowing higher speeds and sensitivity than many current approaches. To sense transverse strain at high speeds in birefringent optical fiber, the two spectral peaks associated with the fiber gratings are tracked individually by locking onto its preferred polarization state.

Therefore, it is an object of the present invention to monitor changes in moisture or chemical content of an environment through measured strain changes.

Another object of the invention is to provide a means of monitoring bond lines for degradation.

Another object of the invention is to provide means to measure changes in several fiber grating sensors at high speed and with high sensitivity simultaneously in a single fiber.

Another object of the invention is to measure transverse strain as well as axial strain at high speed and with high sensitivity.

These and other objects and advantages of the present invention will become apparent to those skilled in the art after considering the following detailed specification including the drawings wherein:

BRIEF DESCRIPTION OF THE DRAWINGS

FIG. 28a and FIG. 28b are diagrams showing different full width half max spectra for grating filters allows for selection of sensitivity and dynamic range.

FIG. 30a and FIG. 30b are diagrams showing the bending of a simply supported beam to induce tension or compression in an attached or embedded grating.

FIG. 35a and FIG. 35b are diagrams showing the application of tension or compression to surface mounted or embedded fiber grating through a pressure (P) differential across the diaphragm.

DETAILED DESCRIPTION OF THE INVENTION

Figure 1:
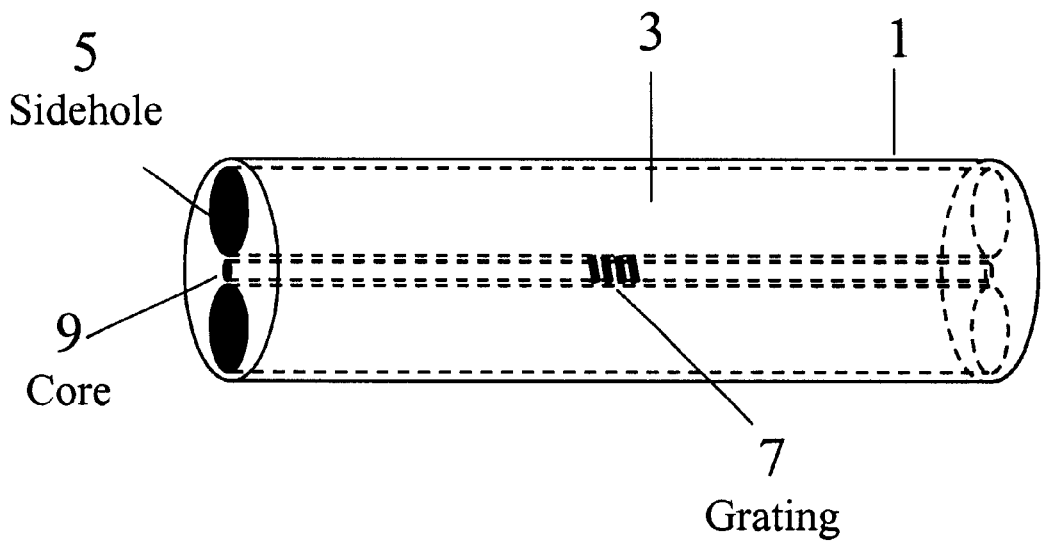
FIG. 1 is a prior art illustration of a grating written onto sidehole fiber.

In the present invention, environmental sensing systems based on fiber gratings are described. The environmental grating sensors may be written onto ordinary single mode or birefringent fiber. For the case where the environmental sensor is subjected to a transverse load, it will behave differently depending on if it is written onto ordinary single mode fiber or onto birefringent fiber. To further increase the sensor's response to a transverse load, voids such as sideholes may be introduced into the fiber. FIG. 1 shows a prior art transverse fiber grating sensor written onto optical sidehole fiber as described in U.S. Pat. Nos. 5,828,059 and 5,841,131. The sidehole transverse fiber grating sensor 1 consists of a length of sidehole fiber 3 that may have sideholes 5. When a grating 7 is written onto the core 9 of the sidehole fiber 3, a single distinct spectral peak results. The sideholes 5 in the fiber may increase the sensor's 1 response to transverse strain.

Figure 2:
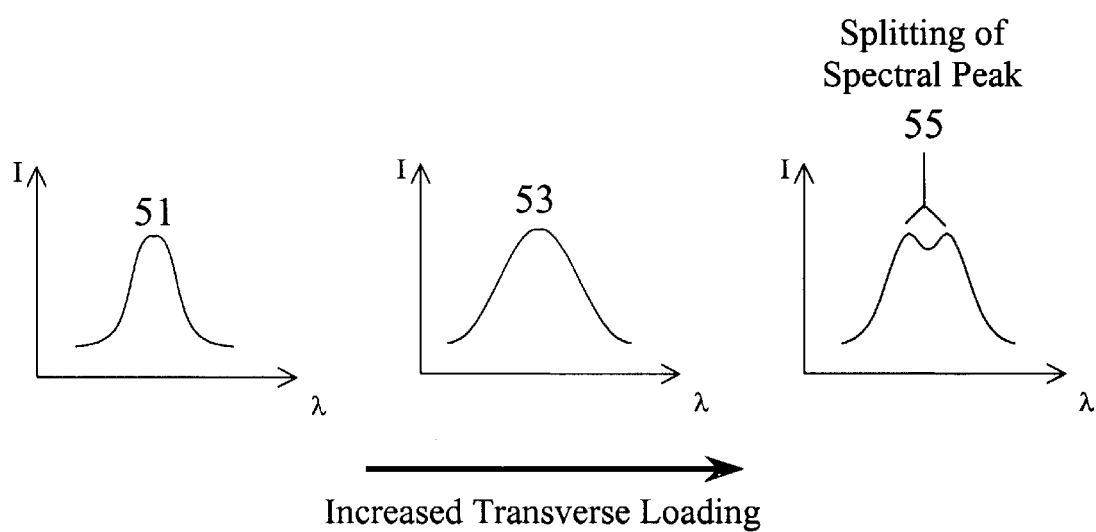
FIG. 2 is a diagram showing the splitting of a spectral peak with transverse loading on grating written onto ordinary single mode fiber.

Gratings written onto some sidehole fiber or ordinary single mode fiber will reflect a single spectral peak in the unloaded case. As the grating on some sidhole or single mode fiber is transversely loaded, the spectral peak will begin to broaden and eventually split as birefringence is induced in the fiber from the external load. FIG. 2 shows a typical spectral response to transverse loading for the case of a single grating written onto non birefringent optical fiber, such as some sidehole fiber. In the unloaded case 51, a single spectral peak results. As the transverse load on the fiber sensor increases, the spectral peak 53 begins to broaden. With further increasing load, the spectral peak begins to split into two distinct spectral peaks 55.

For the case where a grating is written onto birefringent fiber, two spectral peaks are reflected in the unloaded case, one for each polarization state. As the grating written onto birefringent fiber is transversely loaded, the spacing between the two spectral peaks will change.

Figure 3:
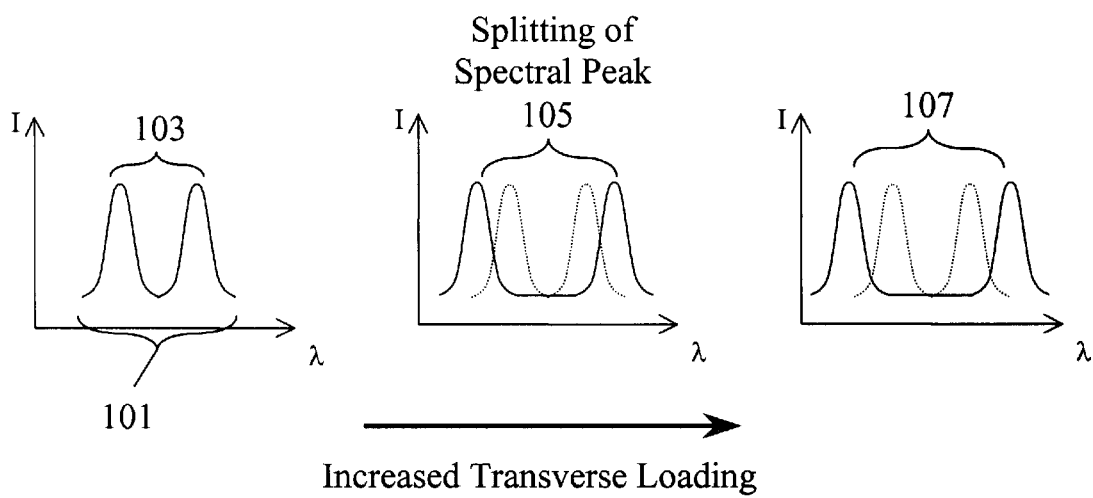
FIG. 3 is a diagram showing the separation of spectral peaks with transverse loading of a grating written onto PM fiber.

FIG. 3 shows a typical spectral response to transverse loading for the case of a single grating written onto birefringent optical fiber. In the unloaded case, two spectral peaks 101 result with a peak separation 103. As the transverse load increases, the separation of the two peaks 105 will increase. With further increasing transverse loading, the spectral peak separation 107 will further increase.

Figure 4:
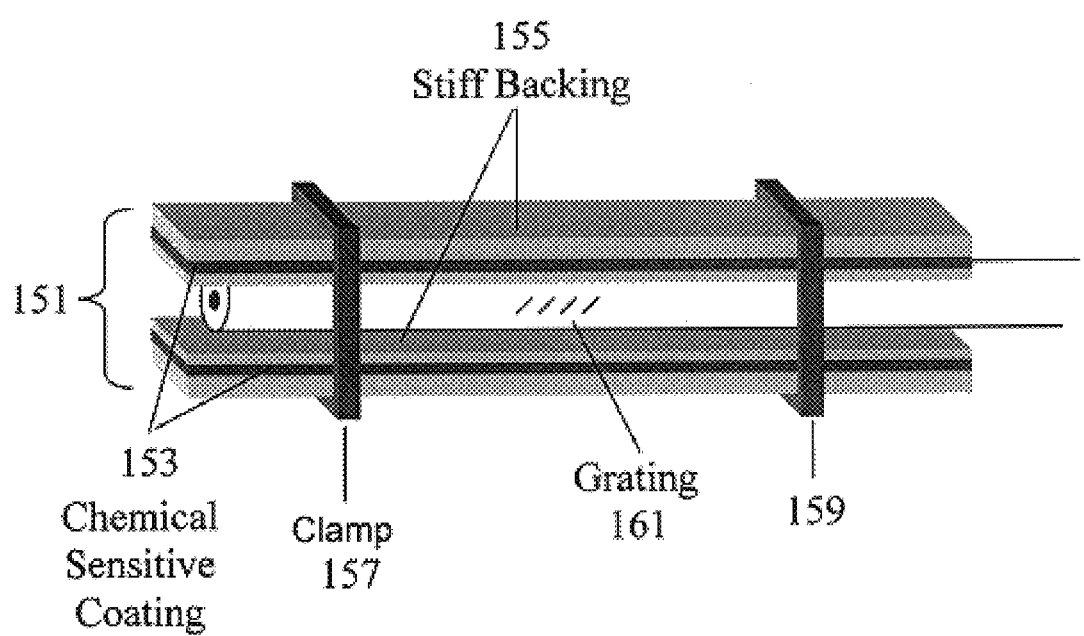
FIG. 4 is an illustration showing the basis of a fiber grating chemical sensor with a chemically sensitive coating attached to plates which are constricted and strain the grating as the coating swells in the presence of the target chemical.

FIG. 4 shows a chemical sensor based on transverse loading of a strain sensor based on a single grating or multiple gratings written onto birefringent or non-birefringent fiber. The chemical sensor 151 consists of a chemical sensitive coating 153 that expands in the presence of the target chemical to be sensed, such as moisture. As the chemical sensitive coating 153 expands, it exerts a force onto some stiff plates 155. The outward expansion is prevented by clamps 157 and 159. This directs the force into the grating sensor 161. The effective result is a transverse strain impending on the grating sensor 161 in the presence of the target chemical. The stiff plates 155 provide a more even loading on the fiber as the chemical sensitive coating 153 expands. The relatively large exposed area of the chemical sensitive coating 153 increases the sensitivity and response time of this chemical sensor.

Figure 5:
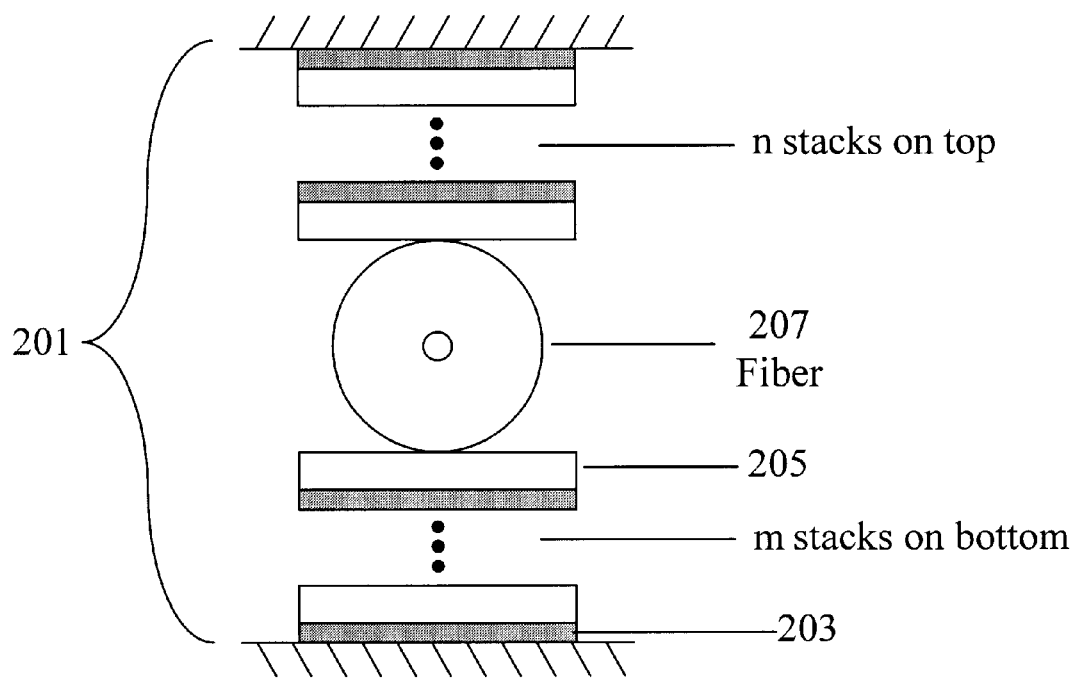
FIG. 5 is an illustration of a chemical sensor employing m and n stacks of a chemical sensitive coating to change sensitivity of sensor

FIG. 5 shows another variation of a chemical sensor where a series of chemical sensitive coatings are cascaded together to increase the amount of force directed into the fiber grating sensor to increase sensitivity. This variation of the chemical sensor 201 consists of multiple stacks of chemically sensitive coating 203 with stiff plates 205. As these multiple sets of chemical sensitive coatings 203 expand in the presence of the target chemical, their combined force is directed into the fiber grating sensor 207. By controlling the quantity n and m of the stacks, the sensitivity of the chemical sensor 201 can be controlled.

Figure 6:
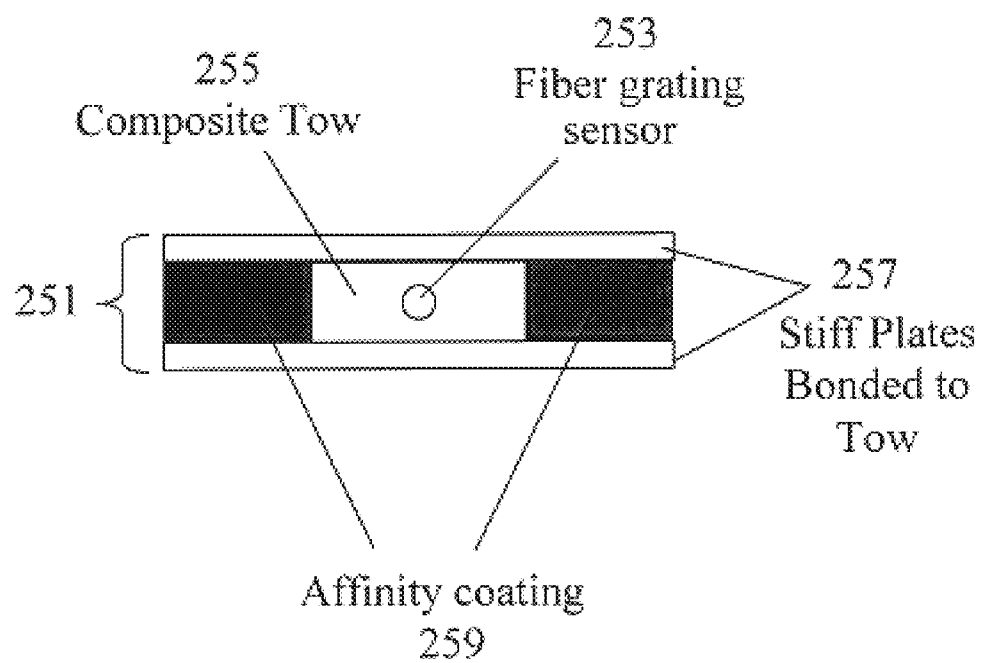
FIG. 6 is an illustration of a fiber embedded into composite tow bonded to stiff plates. As the chemically sensitive coating expands or contracts, the strain state in the fiber grating sensor changes.

FIG. 6 shows another variation of a chemical sensor where the grating sensor is embedded into a piece of composite tow where the force on the fiber is transverse. The chemical sensor 251 consists of a fiber grating sensor 253 that is formed from one or two gratings written onto birefringent or non-birefringent optical fiber. The fiber grating sensor 253 is embedded into a piece of composite tow 255 which can have many functions such as isolating the fiber grating sensor 253 from chemicals that would be damaging to the optical fiber and keeping the orientation of the fiber grating sensor 253 correct for the case where birefringent fiber is used. The composite tow piece 255 is surrounded by stiff plates 257 and chemical sensitive coating 259 (or affinity coating.) As the chemical sensitive coating expands or shrinks in the presence of the target chemical or chemicals, the force exerted on the tow 255 changes and hence the strain on the fiber grating sensor 253 allowing a measurement to be made.

Figure 7:
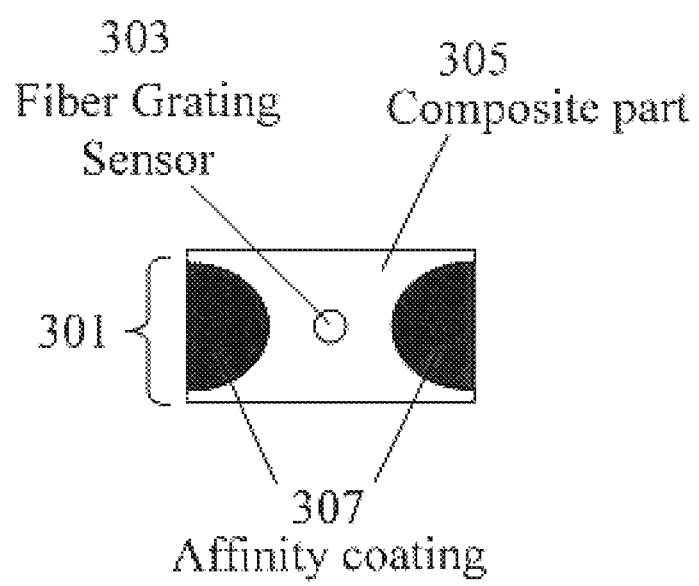
FIG. 7 is an illustration showing a fiber grating embedded into composite part. As the affinity coating changes, the strain on the sensor will change.

FIG. 7 shows another variation of a chemical sensor 301 where the fiber grating sensor 303 is embedded into a composite part 305 with some optimal geometry for the chemical sensitive coating 307 (or affinity coating) to maximize the strain on the fiber grating sensor 303 in the presence of the target chemical or chemicals.

Figure 8:
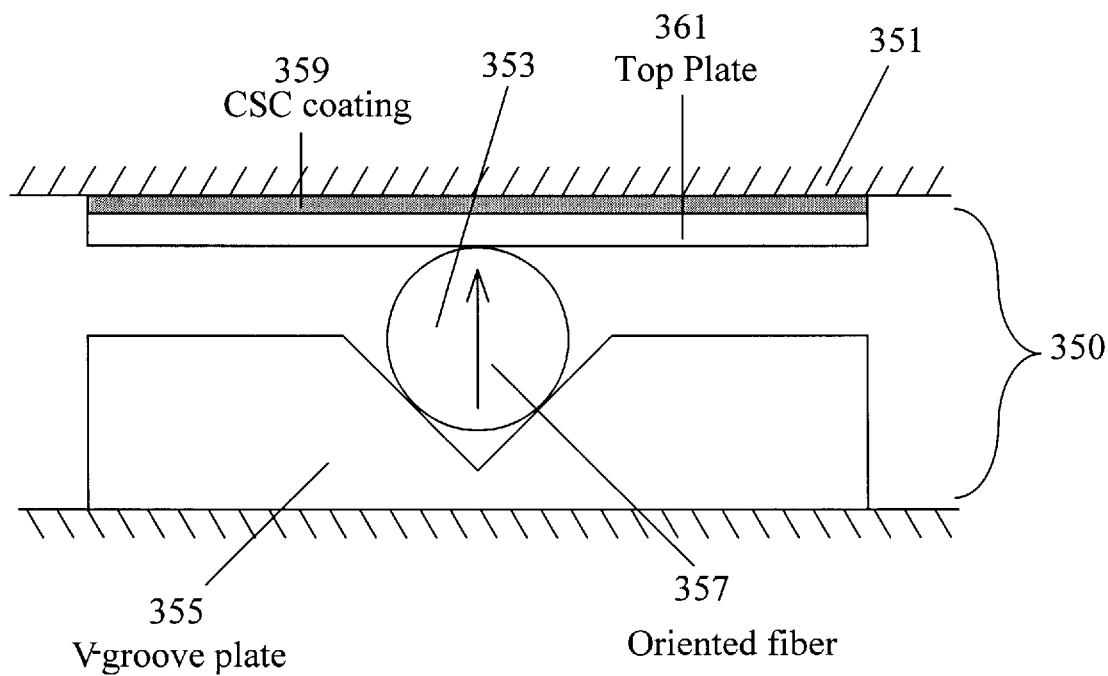
FIG. 8 is an illustration of a fiber grating sensor with a single v-groove plate to prevent fiber rotation.

FIG. 8 shows another variation of a chemical sensor based on a v-groove configuration. This chemical sensor 350 consists of a fiber grating sensor 353 that is formed from a single or multiple gratings on birefringent or non-birefringent fiber placed into a v-groove 355. This plate keeps the fiber in place and can help maintain the proper orientation 357 of the fiber if a grating in birefringent fiber is used. As the chemical sensitive coating 359 expands in the presence of the target chemical or chemicals, it exerts a force on the top plate 361 which transfers the force to the fiber grating sensor 353.

Figure 9:
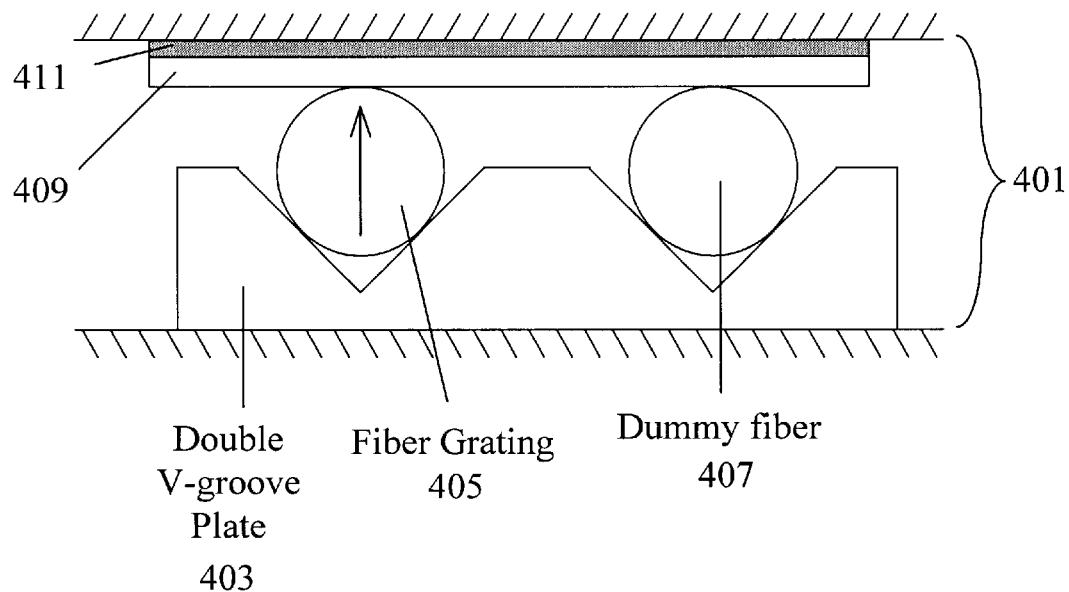
FIG. 9 is an illustration of a fiber grating sensor with a double v-groove design to eliminate possible rocking of the top plate.

FIG. 9 shows another variation of a chemical sensor based on a double v-groove configuration. The chemical sensor 401 consists of a double v-groove plate 403 that holds both the fiber grating sensor 405 and a dummy fiber 407 of the same diameter as the fiber grating sensor but without a grating element. This configuration helps to reduce the rocking effect of the top plate 409 on top of the fiber grating sensor 405 to provide a more consistent loading as the chemical sensitive coating 411 expands in the presence of the target chemical or chemicals. The v-grooves in plate 403 help keep the fibers in place and keep the fiber grating sensor 405 oriented if a birefringent fiber is used.

Figure 10:
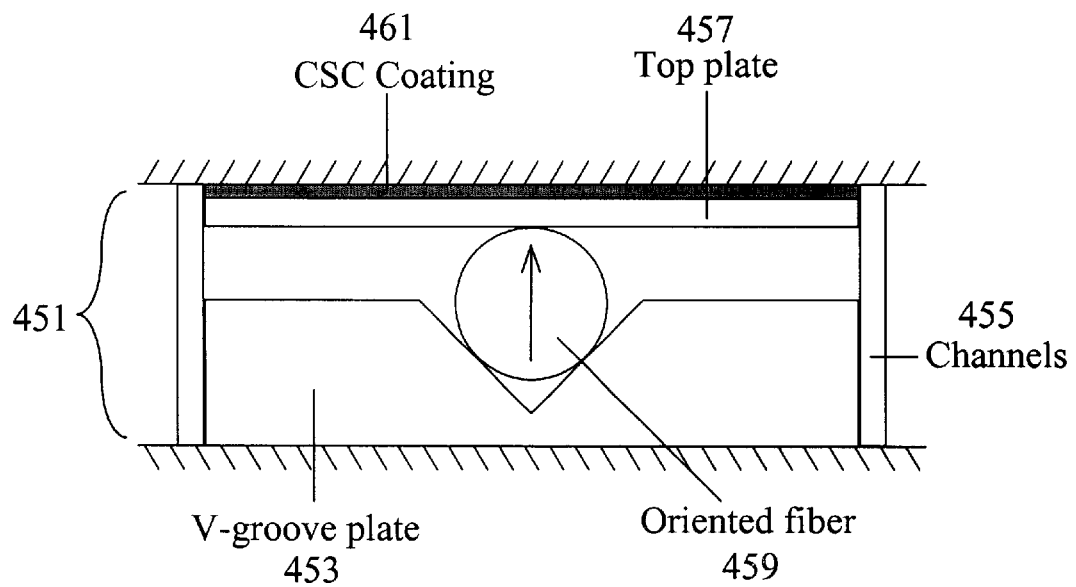
FIG. 10 is an illustration showing the use of channels to prevent the top plate from rocking on fiber.

FIG. 10 shows another variation of a chemical sensor based on a v-groove configuration. The chemical sensor 451 consists of a v-groove plate 453 and side channels 455. The side channels can help keep the top plate level for more consistent loading on the fiber grating sensor 459 as the chemical sensitive coating 461 expands in the presence of the target chemical or chemicals. The v-groove plate 453 helps keep the fiber in place and keeps the fiber grating sensor 459 oriented if a birefringent fiber is used.

Figure 11:
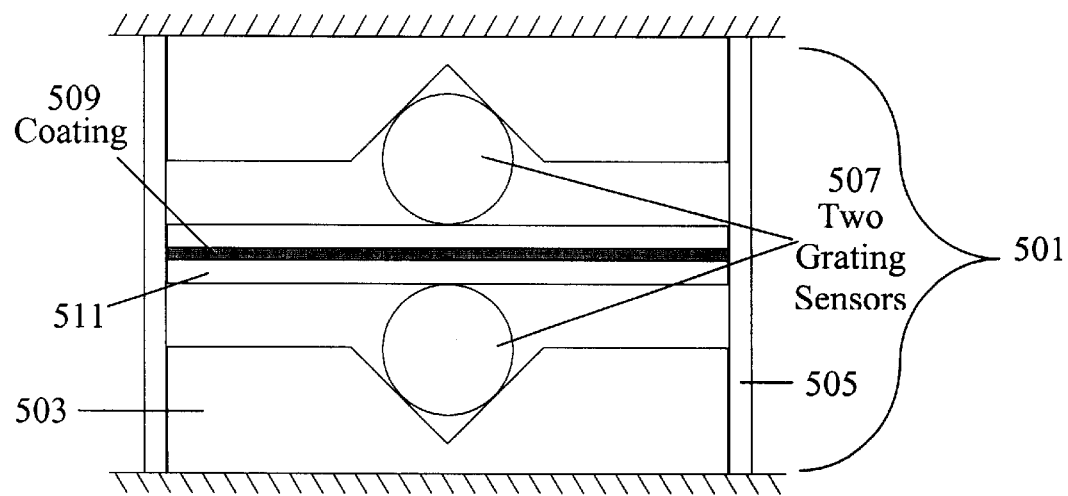
FIG. 11 is an illustration showing multiple sensing points for extended sensing range or higher accuracy through averaging.

FIG. 11 shows another variation of a chemical sensor based on a multiple v-groove configuration to support multiple sensing points. The chemical sensor 501 consists of multiple v-groove plates 503 and side channels 505 that allow for multiple fiber grating sensors 507 to be loaded as the chemical sensitive coating 509 expands against the plates 511. This configuration can extend the sensing range and provide better accuracy by comparing the multiple grating sensors 507 to each other.

Figure 12:
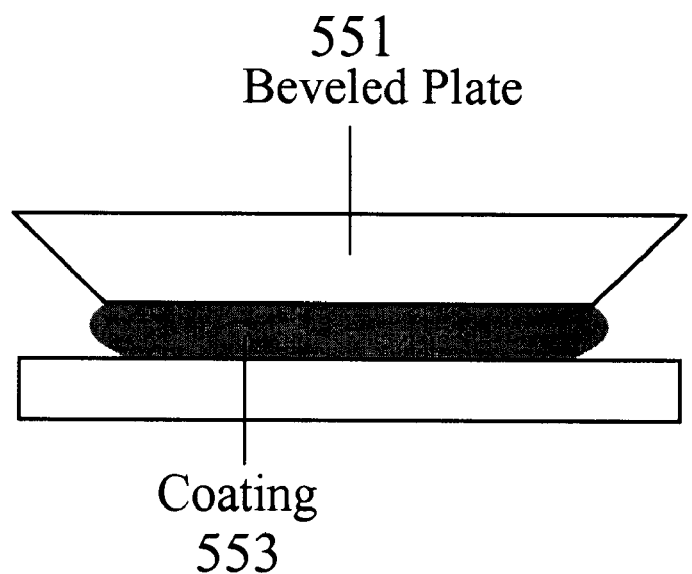
FIG. 12 is an illustration showing the use of beveled plate to increase surface area of exposed coating and/or increase wicking action of target chemical into coating.

FIG. 12 shows how a beveled plate 551 may be used to increase the surface area of the chemical sensitive coating 553 and increase the wicking action of the target chemical or chemicals into the coating. This could increase sensitivity and decrease response times of the chemical sensor.

Figure 13A:
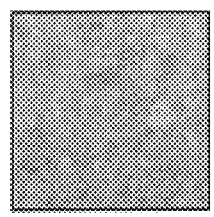
FIG. 13a, FIG. 13b, and FIG. 13c, show different methods to increase target chemical absorption through the transducer plates.
Figure 13B:
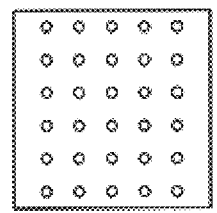
Figure 13C:
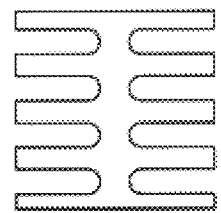

FIG. 13a, FIG. 13b, and FIG. 13c show plates of differing permeability 601 and holes 603 or slots 605 can be used to increase the volume and rate of absorption of the target chemical into the chemical sensitive coating.

Figure 14:
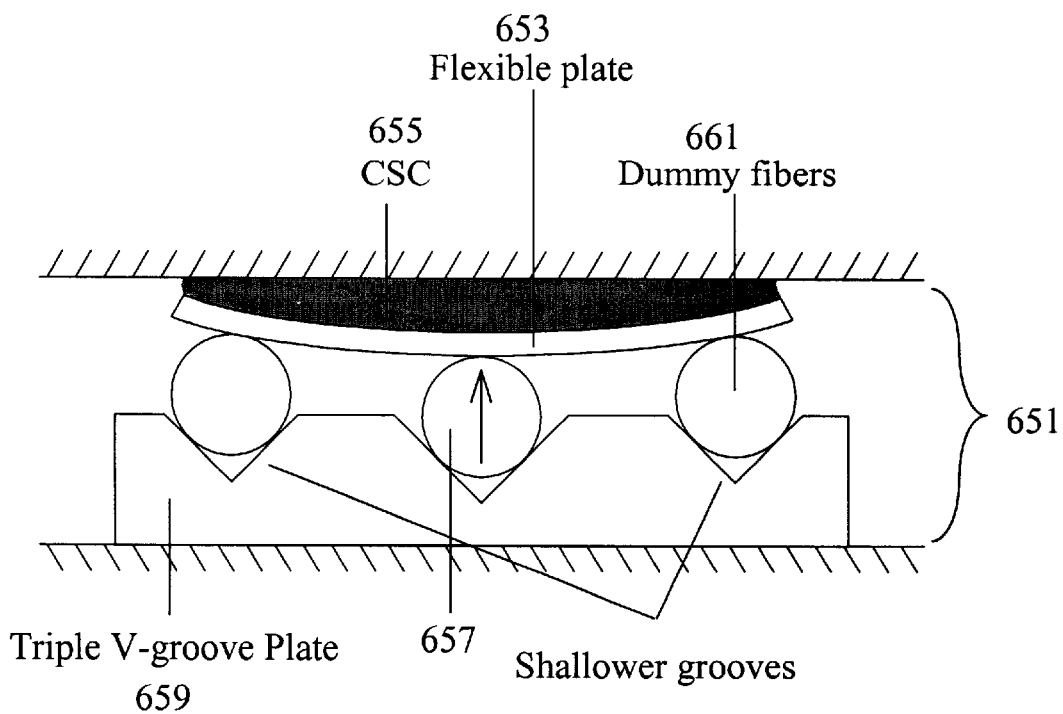
FIG. 14 is an illustration showing how a flexible plate may be used to account for inconsistent swelling of the chemically sensitive coating.

FIG. 14 shows another variation of a chemical sensor 651 based on a flexible plate 653 to transfer the load from the chemical sensitive coating 655 to the fiber grating sensor 657 which can consist of one or more gratings written onto birefringent or non-birefringent fiber. The multiple v-groove plate 659 can hold multiple dummy fibers 661 to provide different loading schemes for the flexible plate 653. The flexible plate 653 allows for inconsistent swelling of the chemical sensitive coating 655.

Figure 15:
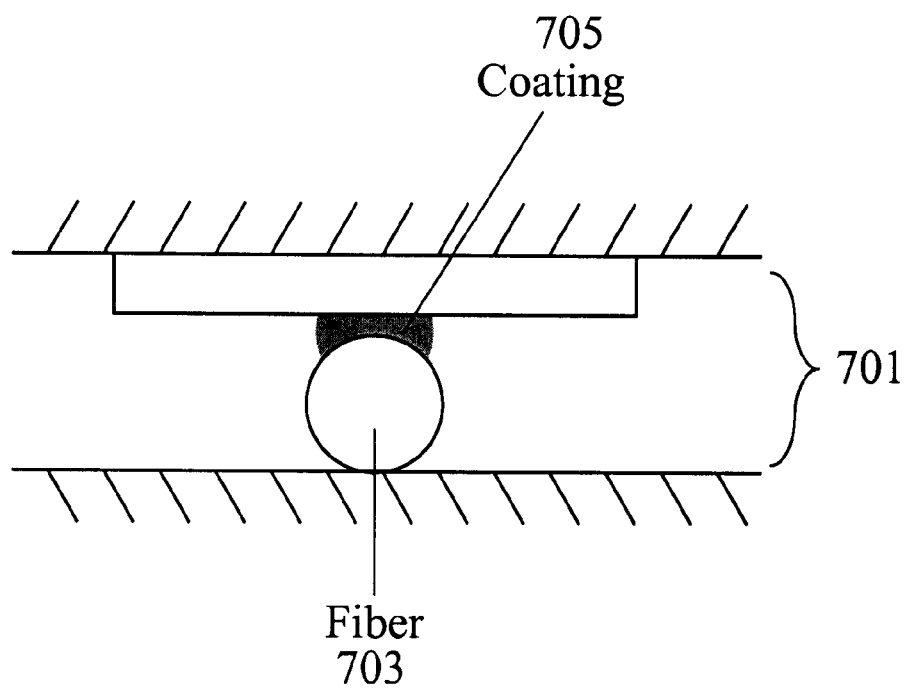
FIG. 15 is an illustration showing the placement of the coating directly on the fiber.

FIG. 15 shows another variation of a chemical sensor where the chemical sensitive coating is placed directly on the fiber. The chemical sensor 701 consists of a fiber grating sensor 703 that can consist of a single or multiple gratings on birefringent or non-birefringent fiber. A chemical sensitive coating 705 exerts a transverse force on the fiber grating sensor 703 as it swells in the presence of a target chemical or chemicals.

Figure 16:
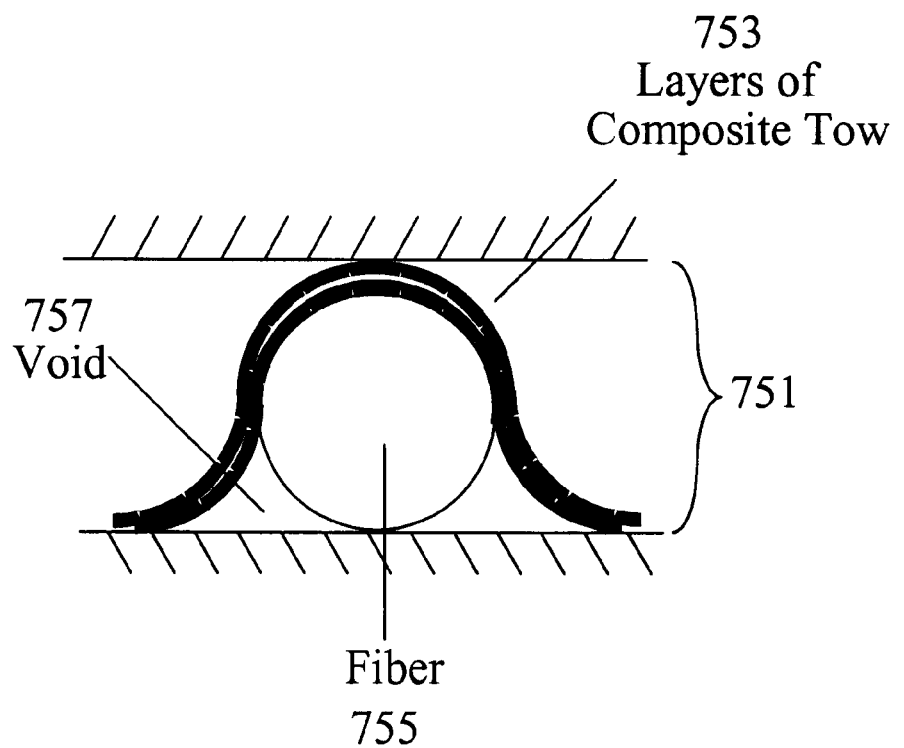
FIG. 16 is an illustration showing the placement layers of chemically reactive composite tow over the fiber which may load the fiber in transverse strain when exposed to the target chemical. For example, some composite tows may swell in the presence of moisture. The void may be used to ensure a clean transverse load.

FIG. 16 shows another variation of a chemical sensor where composite tow that is reactive to a target chemical is used to transversely load the fiber grating sensor. The chemical sensor 751 consists of chemically reactive composite tow 753 which expands or shrinks in the presence of the target chemical or chemicals to transfer a load to the fiber grating sensor 755. The fiber grating sensor 755 can consist of one or more gratings on birefringent or non-birefringent fiber. A void 757 can be used to provide clean transverse loads on the fiber grating sensor 755.

The above descriptions describe a transverse strain applied to the grating sensor on the presence of a target chemical such as moisture. Another application to the transverse strain sensing capability of the fiber grating written onto either ordinary single mode fiber or birefringent fiber is the direct measurement of transverse strain and strain gradients when embedded into a structure such as an adhesive joint.

Figure 17:
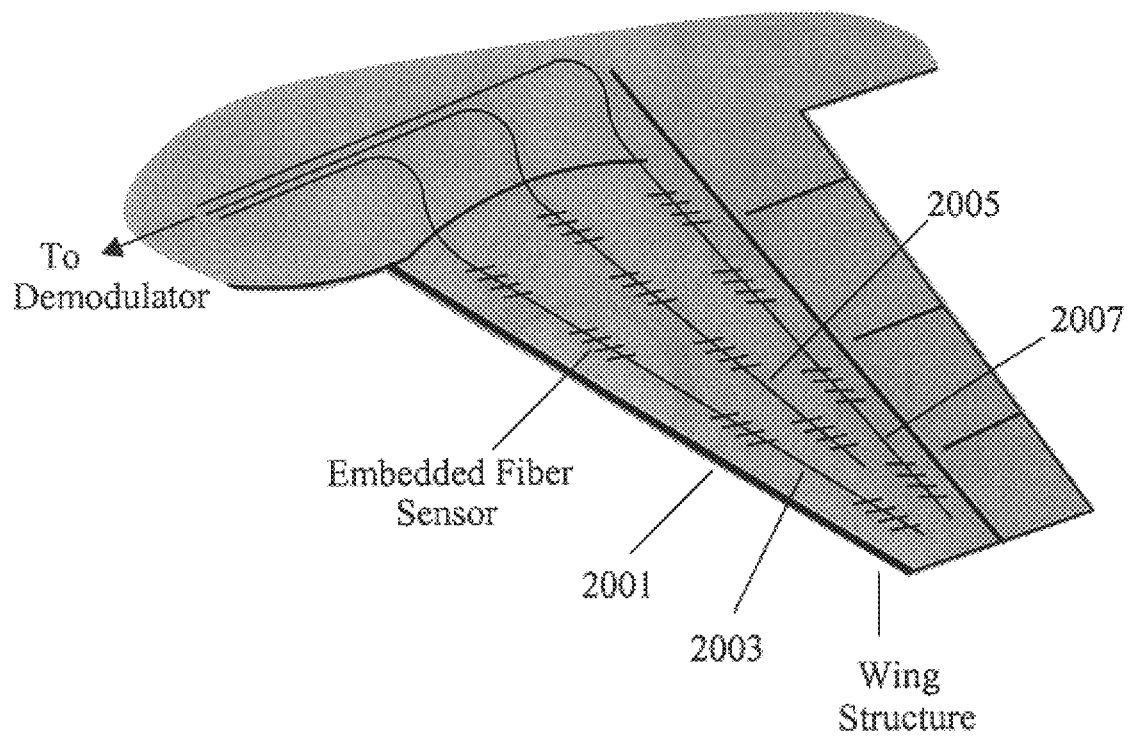
FIG. 17 is an illustration showing the wing of an aircraft where transverse fiber grating strain sensors are used to monitor the adhesive joints.

One key problem facing structural designers is the ability to be able to monitor the structural integrity of adhesive joints. While these joints are used in many types of construction there is very strong motivation to use these in aerospace applications to improve strength and reliability while lowering construction costs and overall weight. FIG. 17 is a diagram of a wing structure 2001 that may be made of lightweight composite material. The wing 2001 is made up of sections that may be adhesively bonded and strings of fiber grating sensors 2003, 2005 and 2007 can monitor these bonds.

Figure 18:
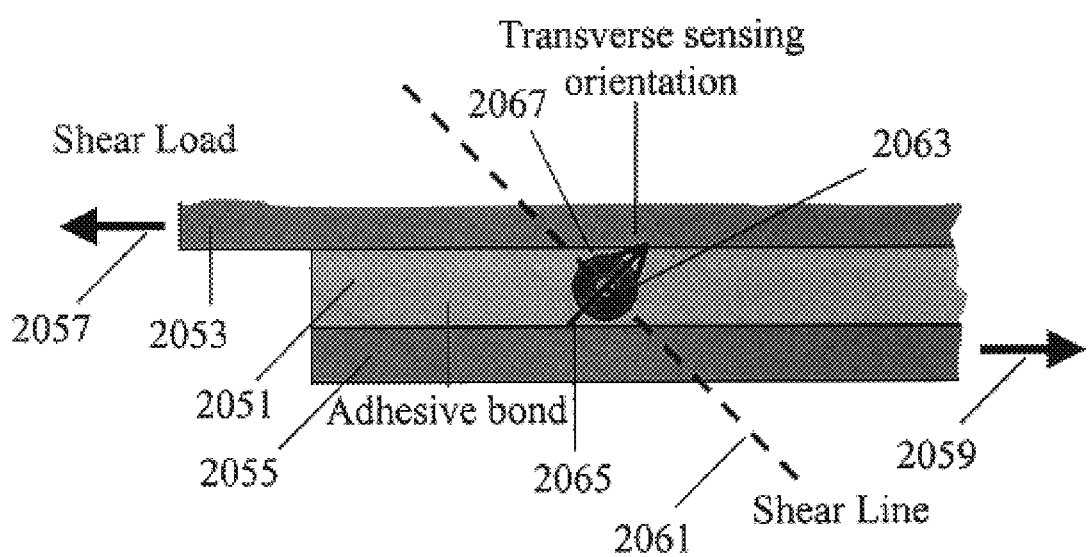
FIG. 18 is an illustration of a transverse fiber grating strain sensor embedded directly into the adhesive of a bond to monitor the health of the bond.

FIG. 18 shows an adhesive bond 2051 that joins two parts 2053 and 2055. When the parts 2053 and 2055 are pulled apart by the forces 2057 and 2059 a shear load is formed along the line 2061. A multi-axis fiber grating sensor 2063 can be placed along the length of the adhesive bond 2051 with its traverse axes 2065 and 2067 aligned along the shear line 2061 and orthogonal to it so that shear strain induced in the bond may be measured. While the diagram of FIG. 18 shows the fiber grating sensor 2063 place interior to the adhesive joint 2051 other positions are possible.

Figure 19:
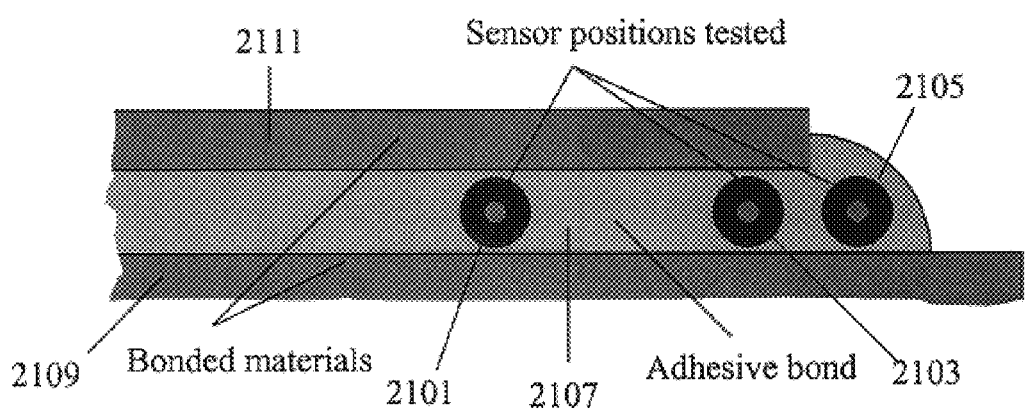
FIG. 19 is an illustration of three different embedding locations of transverse strain sensors into an adhesive joint.

FIG. 19 shows the placement of three fiber grating sensing fibers 2101, 2103 and 2105 in the adhesive bond 2107, between the bonded materials 2109 and 2111. Note that the fiber grating sensor 2101 is placed well into the adhesive bond 2107 while the fiber grating sensor 2103 is placed near the edge and the fiber grating sensor 2105 is placed in the exterior. When an adhesive bond starts to fail under shear load it usually starts on the edge. So the placement of the fiber grating 2105 just exterior to the adhesive bond 2107 is in the area where failure is likely to first occur. This arrangement is also useful for enabling a system that could be used as a failure warning mechanism for existing adhesive bonds as an exterior bead of adhesive could be added and oriented fibers placed at the edge of a bond to provide a health monitoring system as a retrofit to existing structures or to simplify fabrication of new structures.

Figure 20A:
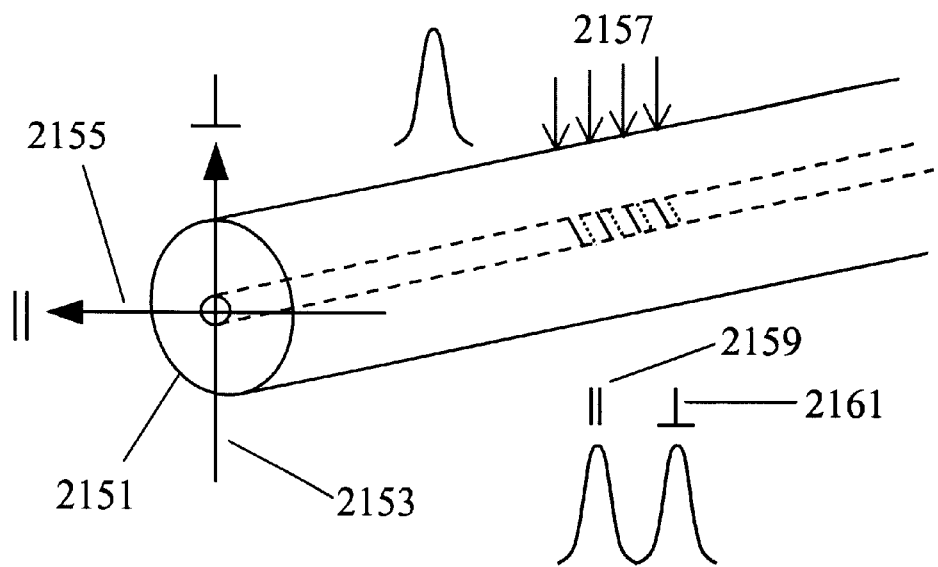
FIG. 20a is a diagram showing uniform loading with clean spectral peaks and FIG. 20b shows non-uniform loading with more complex spectral profiles of gratings written onto polarization maintaining fiber.
Figure 20B:
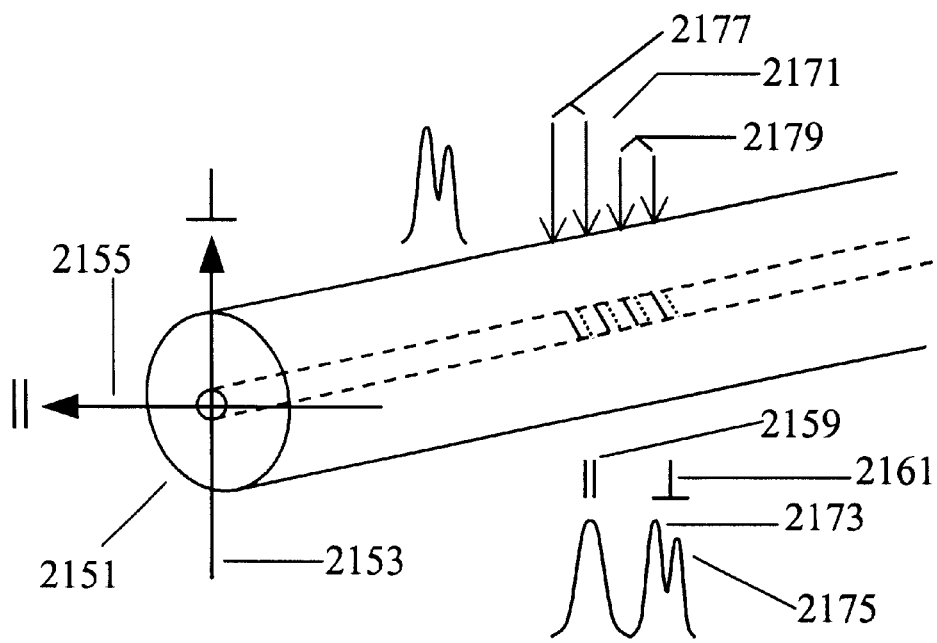

FIG. 20a and FIG. 20b are diagrams that are used to illustrate the action of a multi-axis fiber grating sensors that is placed inside of a material that is subject to strains and eventual failure. In particular this would be the case of an adhesive bond that is strained until it fails. In FIG. 20a a multi-axis fiber grating sensor 2151 with transverse sensing axes 2153 and 2155 is subject to a uniform loading force 2157 along the axis 2153. When this type of uniform transverse loading occurs two spectral output peaks 2159 and 2161 occur that are smooth curves whose central wavelengths shift so that the two peaks 2159 and 2161 move apart or together with wavelength difference. FIG. 20b illustrates the case of the fiber optic grating sensor 2151 when the transverse loading force 2171 is not uniform. This would be the case for example when an adhesive bond under load starts to break apart along the line of the axis 2153. In this case the spectral peak 2161 in FIG. 20b will split into two wavelength peaks 2173 and 2175. The spectral separation between the peaks 2173 and 2175 provides a quantitative means to measure the difference in load along the axis 2153 generated by the force 2171 that consists of the load regions 2177 and 2179. The intensity of the peaks 2173 and 2175 provide a means to determine the lengths of the load regions 2177 and 2179. In the case of FIG. 20b the regions are nearly equal in length resulting in the two peaks being nearly equal in intensity.

Figure 21A:
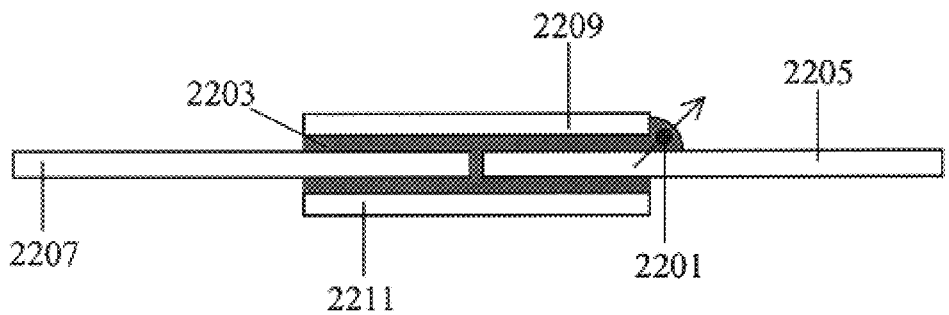
FIG. 21a shows [data taken from] a transverse fiber grating strain sensor embedded into an adhesive joint that was placed under load.
Figure 21B:
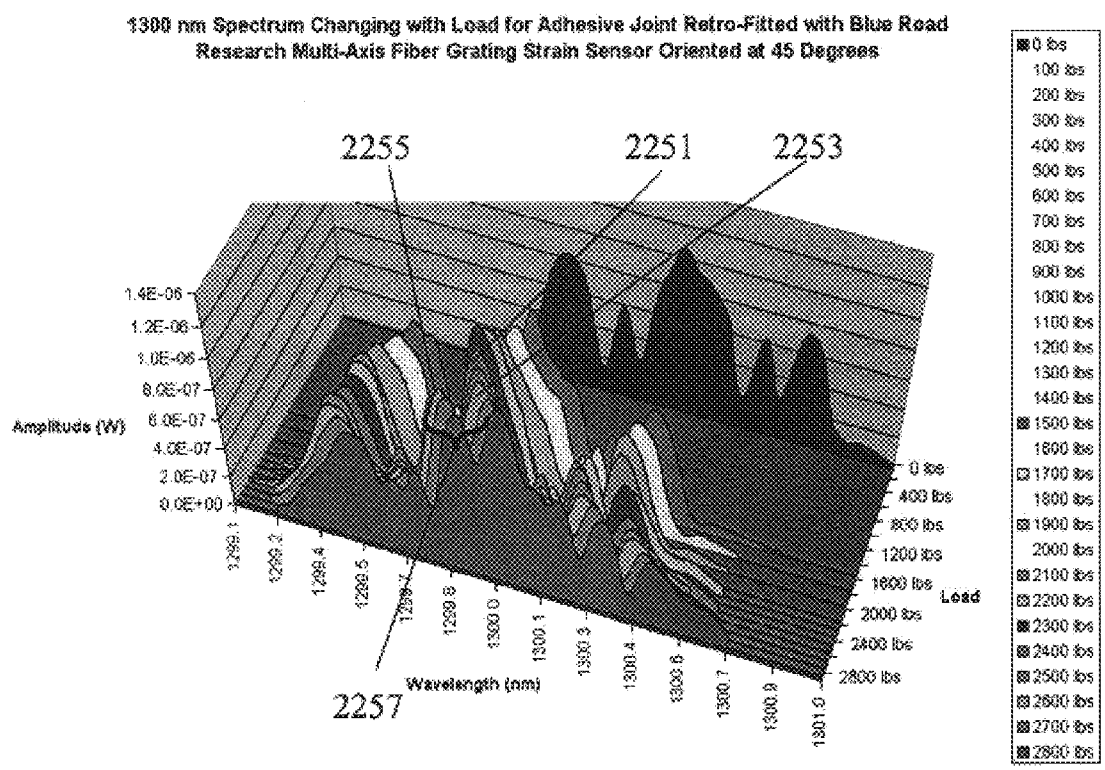
FIG. 21b shows data taken from the transverse fiber grating strain sensor.

FIG. 21b is a diagram showing experimental results that were obtained by using a multi-axis fiber grating to monitor an adhesive bond. Additional experimental data on joints that were tested using this technology can be found in W. L. Schulz, E. Udd, M. Morrell, J. Seim, I. Perez, A. Trego, "Health Monitoring of an Adhesive Joint using a Multiaxis Fiber Grating Strain Sensor System", SPIE Proceedings, Vol. 3586, p. 41, 1999. In FIG. 21a the multi-axis fiber grating sensor 2201 is oriented at 45 degrees relative to the adhesive bond 2203, and the plates 2205, 2207, 2209, and 2211. The fiber grating sensor 2201 is placed at the edge of the adhesive bond 2203 so that it can be used to predict the onset of failure during loading. The graph shown in FIG. 21b illustrates the spectral reflective output of the multi-axis fiber grating sensor 2201 of FIG. 21a as a function of load being applied by an Instron machine to the plates 2205 and 2207 that are being pulled apart. Note that after a certain load level is applied of approximately 1800 pounds the two major spectral peaks start to move apart with continuing increases in load. At about 2400 pounds the major spectral peak 2251 splits into the two peaks 2253 and 2255. The spectral separation 2257 between these two peaks 2253 and 2255 is approximately 0.2 nm. Since the response of the multi-axis fiber grating sensor in the transverse direction is approximately a factor of 3 lower than in the axial direction a change of 0.2 nm corresponds to a change of about 600 micro-strain. The intensity of the two split peaks 2253 and 2255 being nearly equal means that along the axis of shear strain (along which one of the transverse axes of the multi-axis fiber 2201 is aligned as shown in FIG. 21a) about half the fiber grating length has been unloaded by about 600 micro-strain while the other half of the grating remains at the higher load level. Since the fiber grating used in this case is about 5 mm in length this means that approximately 2 mm of the fiber grating sensor 2201 along the shear strain axis has been unloaded due to a change in the adhesive bond 2203. As the adhesive bond 2203 is subject to increasing load additional peaks arise with greater intensity indicating additional breakage and the overall spectral profile 2257 moves toward longer wavelengths indicating axial loading is occurring. Thus FIG. 21a and FIG. 21b illustrate the ability of a multi-axis fiber grating sensor 2201 to measure transverse strain which because of its orientation at 45 degrees measures shear strain in the adhesive bond 2203. This figure also illustrates the ability to measure changing transverse strain gradients indicative of break up of the adhesive bond 2203 and axial strain changes that occur in this example before failure of the bond 2203.

Figure 22:
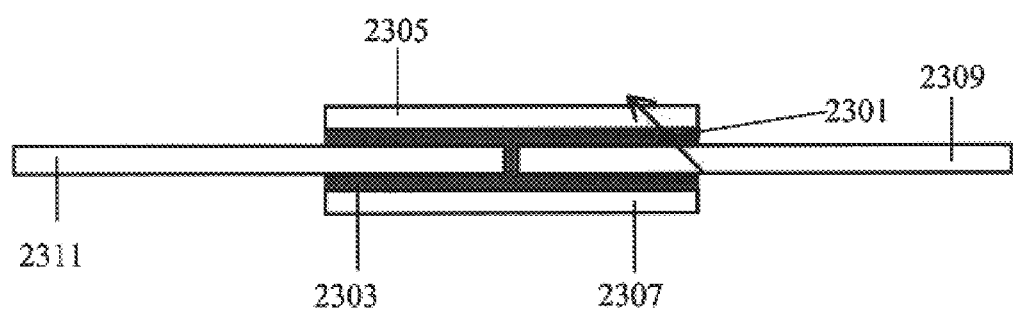
FIG. 22 is an illustration of a dual axis fiber grating sensor embedded into an adhesive joint with its transverse strain sensing axis aligned at −45 degrees.
Figure 23:
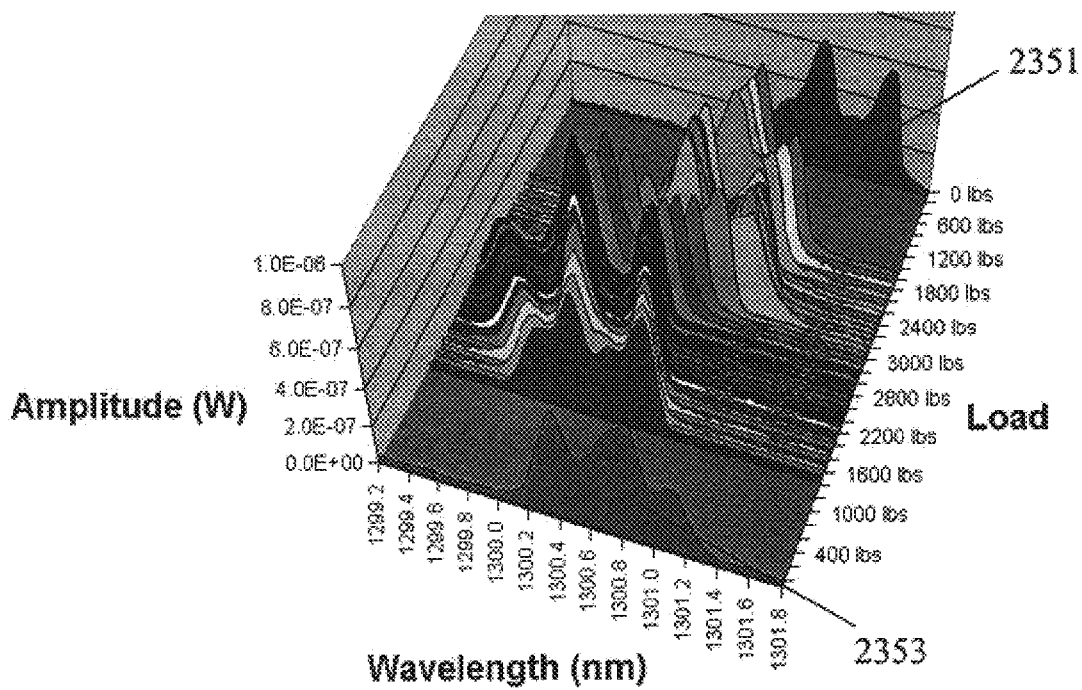
FIG. 23 shows data taken from a transverse fiber grating strain sensor embedded into an adhesive joint undergoing plastic deformation.
Figure 24:
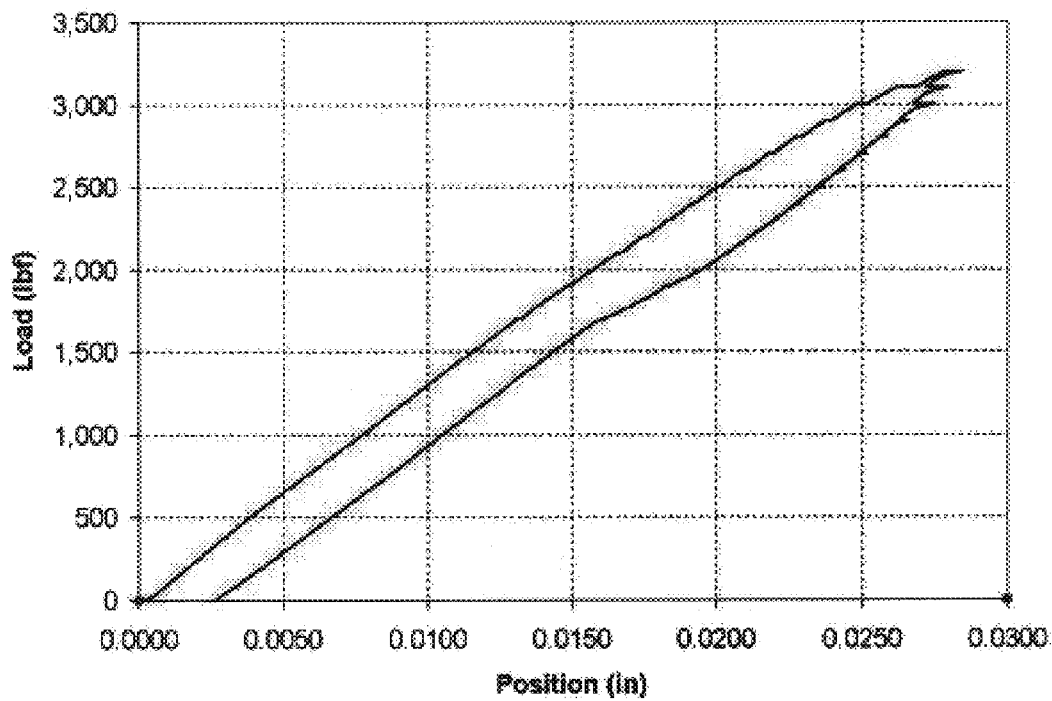
FIG. 24 shows data of the displacement of the instrumented adhesive joint from FIG. 23.

In addition to monitoring break up of adhesive bonds and failure it is possible to use multi-axis fiber grating sensors to monitor plastic deformation of an adhesive bond under cycling. FIG. 22 shows the position of the multi-axis fiber grating sensor 2301 that is oriented at −45 degrees relative to the adhesive bond 2303 and the plates 2305, 2307, 2309 and 2311. As the plates 2311 an 2309 and pulled apart with increasing force and then unloaded the multi-axis fiber grating sensor 2301 can be used to monitor the adhesive bond 2303 in the neighborhood of its placement. FIG. 23 is a graph showing the displacement of the major spectral peaks during a cycle of the adhesive bond 2303. The spectral profile 2351 shows the original spectrum after the multi-axis fiber grating sensor 2301 after placement in the adhesive bond 2303 but before loading. In this particular case after the adhesive bond 2303 was cycled it did not fail but the unloaded spectra after the cycle 2353 reflects a change in the strain fields interior to the adhesive joint 2303. FIG. 24 illustrates the displacement of the plates 2309 and 2311 by an Instron loading machine during testing. Note that the adhesive joint 2303 has been plastically deformed during this cycle as was expected as the cycle was beyond the load expected to fail the part. The spectral profiles of FIG. 23 illustrate this process.

Figure 25:
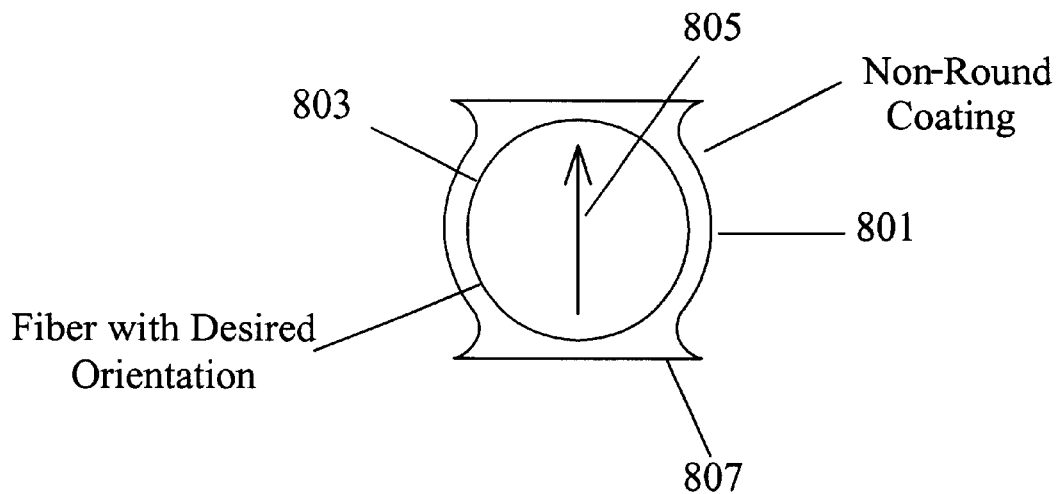
FIG. 25 is an illustration of a non-round coating on fiber to prevent rolling and maintain desired orientation.
Figure 26:
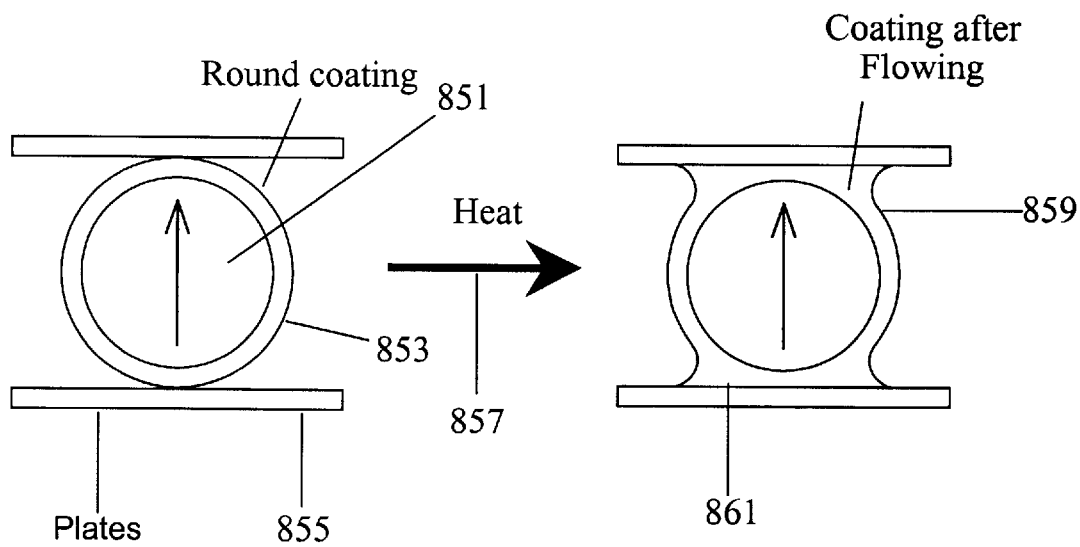
FIG. 26 is an illustration of forming a non-round coating using heat.

In the above sensor configurations, one possible configuration is to use one or more fiber gratings written onto birefringent fiber. The polarization axes associated with the birefringent fiber require that the fiber grating sensor be placed in a known orientation in order to maximize the sensitivity of the sensor's response to a transverse load. FIGS. 25 and 26 describe one possible method of controlling the orientation of a fiber grating sensor written onto birefringent fiber.

FIG. 25 shows a method to control the orientation of a fiber grating sensor based on birefringent fiber. In this case, a non-symmetric coating 801 is placed over the fiber grating sensor 803. The orientation of the polarization axes of the fiber grating sensor 805 can be controlled by placing the flats 807 of the coating in the desired orientation.

FIG. 26 shows how the non-symmetric coating of FIG. 25 can be manufactured. The process begins with a fiber of known orientation 851 with a round fiber coating 853 that will melt with enough heat placed between two plates 855. As the plates are heated 857, the coating 859 will begin to melt and flow and form flats 861 where the coating touches the plates 855.

In many areas where environmental sensing is required, there is a desire for high sensitivity and multiple sensing points. For this reason, a demodulation system with high sensitivity and a large multiplexing potential is needed. In the figures below, several systems are described that enhance the capability of a fiber grating demodulation system using spectral filters described in U.S. Pat. Nos. 5,380,995 and 5,397,891.

Figure 27:
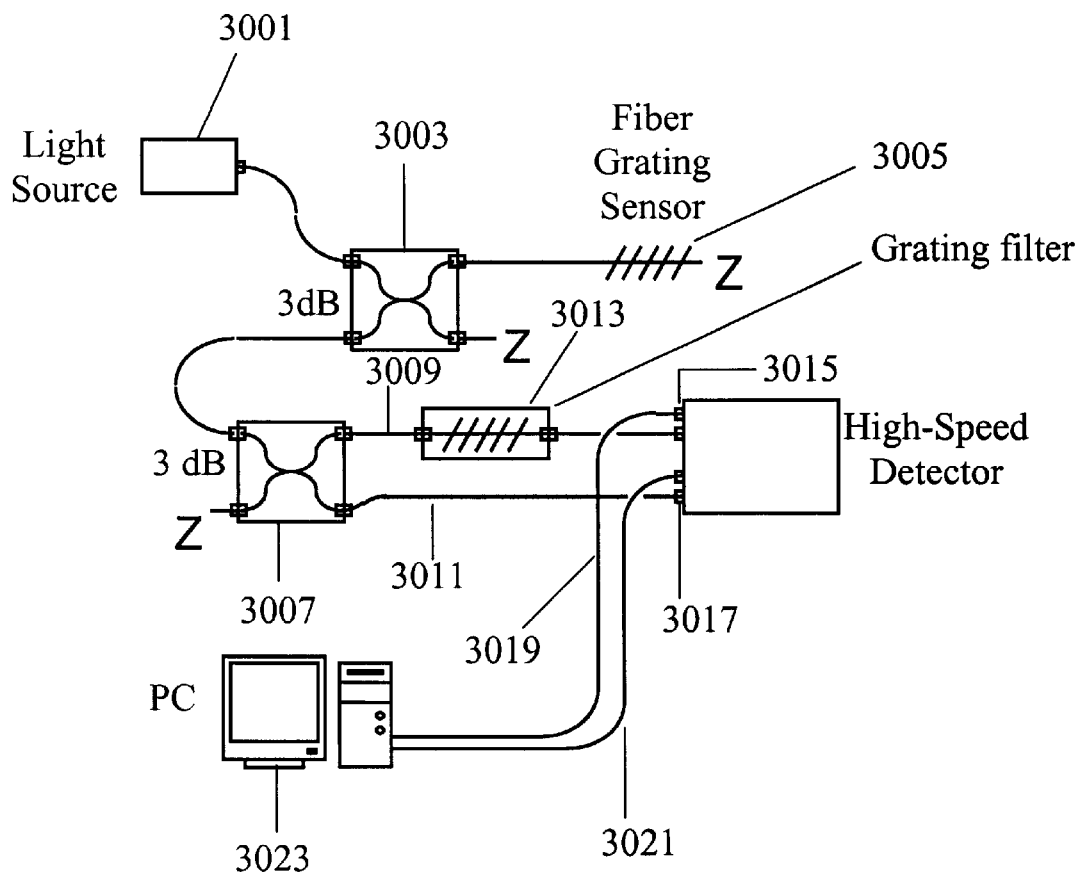
FIG. 27 is a diagram of a prior art high-speed demodulation system employing a grating filter to demodulate a grating sensor.

FIG. 27 shows a prior art fiber grating demodulation system using spectral filters described in U.S. Pat. Nos. 5,380,995 and 5,397,891. The fiber grating demodulation system consists of a broadband light source 3001 that directs broadband light through a beam splitter 3003 and to a fiber grating sensor 3005. The fiber grating sensor 3005 reflects a spectral peak based on the strain on the grating that travels back through beam splitter 3003 and is then directed to a second beam splitter 3007 where it is split between lines 3009 and 3011. The spectral peak traveling along line 3009 travels through a fiber grating filter 3013 that converts the spectral information into an amplitude based signal. The spectral peak then travels from the grating filter 3013 to the detector 3015. The spectral peak in line 3011 travels directly to the high-speed detector 3017 to provide a reference measurement. The detector then outputs two voltages 3019 and 3021 that can be acquired by a data acquisition system 3023.

FIG. 28a and FIG. 28b show typical spectral profiles from a grating written onto non-birefringent fiber. This is one possibility for the fiber grating filter described in FIG. 25. In order to adjust the sensitivity of the fiber grating filter, gratings of different widths may be used to control the slope of the spectral profile. If a narrower grating is used as a filter, its spectral profile 3051, shown in FIG. 28a, will give more sensitivity due to its steeper slope, but will give less dynamic range for the sensor to sweep across. If a wider grating is used as a filter, its spectral profile 3053 will give a shallower slope, for decreased sensitivity, but a wider dynamic range, shown in FIG. 28b.

Figure 29A:
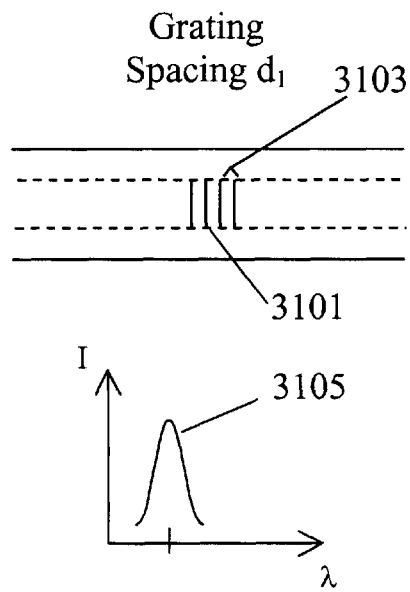
FIG. 29a and FIG. 29b are diagrams showing how a change in the periodic spacing of the perturbations of the index of refraction, or grating spacing, changes the spectral position of the grating.
Figure 29B:
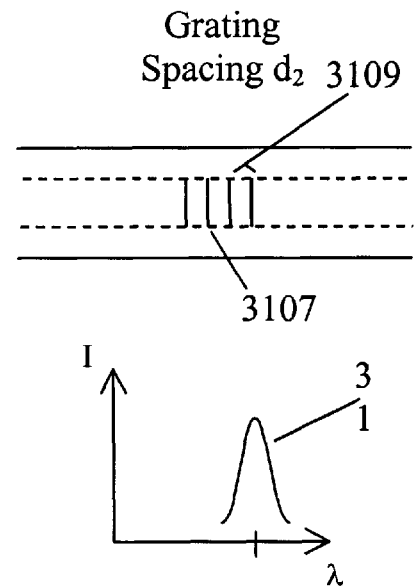

FIG. 29a and FIG. 29b each show a typical response of a fiber grating sensor to an axial load. The grating under no load 3101, shown in FIG. 29a, will have a grating spacing 3103 resulting in a spectral peak at a lower center wavelength 3105. As the fiber grating sensor is axially strained 3107, the grating spacing 3109 results in a spectral peak at a higher center wavelength 3111, shown in FIG. 29b. This shows how the grating sensor will sweep across the grating filter in the system described in FIG. 27.

When fiber grating sensors are installed onto or embedded into structures, many times the initial strain state is different than it was for the uninstalled sensor due to such mechanisms as residual stress. This initial tensile or compressive force results in the fiber grating sensor's initial spectral peak center to be at a different wavelength than the unstrained sensor. Referring back to the demodulation system of FIG. 27, if the spectral filter does not match up spectrally with the fiber grating sensor, then there will be no measurable change in amplitude as the sensor is modulated. For this reason, a tunable grating filter may be needed to ensure that the spectral filter matches up with the initial state of the installed sensor. The following figures describe methods for straining a fiber grating and thus providing a tunable grating filter.

FIG. 30a and FIG. 30b show a tunable filter concept where a fiber grating sensor is attached to or embedded into a simply supported 3131 flexing beam 3133 above the neutral axis of the beam. As the beam is bent up 3135, FIG. 30a, or down 3137, FIG. 30b, the grating on the beam will be subjected to tension or compression allowing for a filter that can be tuned to both higher and lower wavelengths. The beam can also be supported other ways, such as fixed, etc.

Figure 31A:
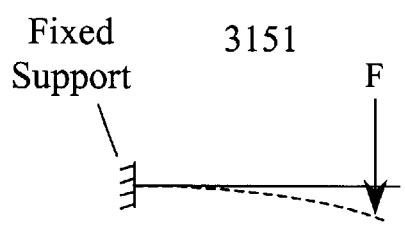
FIG. 31a and FIG. 31b are diagrams showing a cantilever configuration for inducing tension or compression in an attached or embedded grating.
Figure 31B:
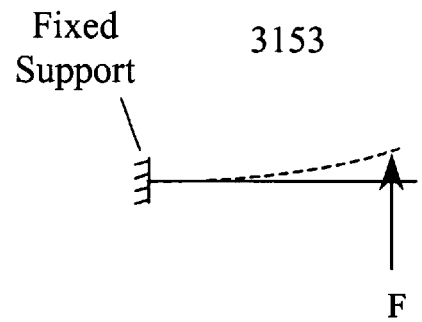

FIG. 31a and FIG. 31b show a tunable filter concept utilizing a bending beam with a grating attached onto or embedded into the beam above the neutral axis of the beam. As the beam is bent up 3151, FIG. 31a, or down 3153, FIG. 31b, the grating on the beam will be subjected to tension or compression.

Figure 32:
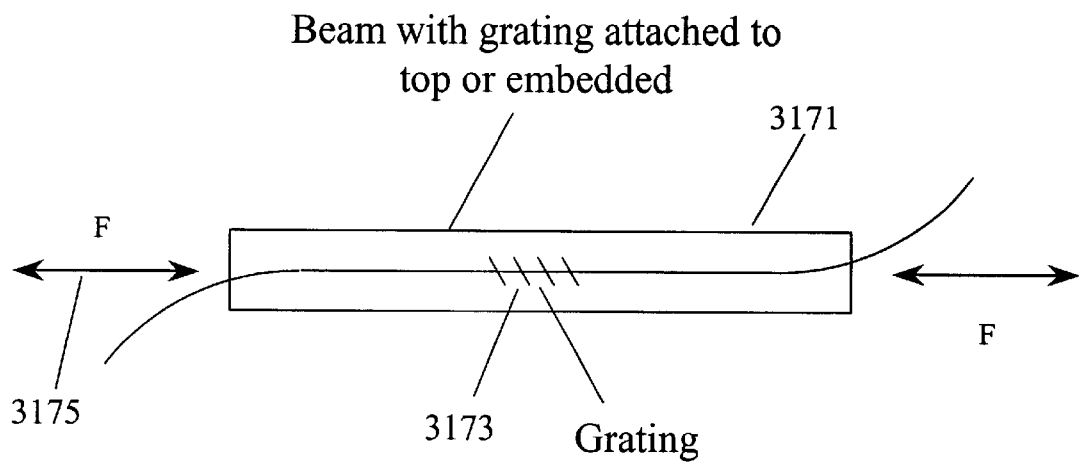
FIG. 32 is a diagram showing the stretching or compressing of a beam with force (F) to induce tension or compression in grating.

FIG. 32 shows a tunable filter concept utilizing a beam 3171 with a grating 3173 attached onto or embedded into the beam. As the beam is stretched or compressed with a force 3175, the fiber grating will be subjected to tension or compression and thus can be tuned to higher or lower wavelengths.

Figure 33:
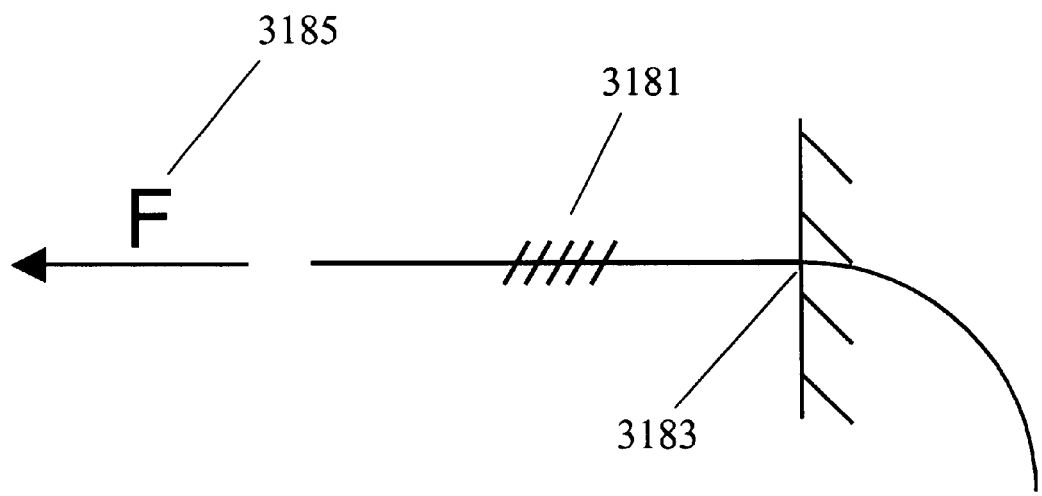
FIG. 33 is an illustration of a tunable grating filter requiring only one direction of tuning as the initial filter wavelength is lower than that of the sensor allowing it to be tuned into the range of the sensor.

FIG. 33 shows a tunable filter concept where a fiber grating 3181 is fixed at a point along its length 3183. A force 3185 pulls on the grating to induce tension and thus a spectral shift to a higher wavelength. The fiber grating 3181 is written at a lower wavelength than is expected for the installed fiber grating sensor. An example of this would be to use a fiber grating filter in this configuration at 1297 nanometers for demodulating a fiber grating sensor with nominal wavelength at 1300 nanometers. This would allow for the tunable filter to match up with the fiber grating sensor by only having to tune it in one direction.

Figure 34:
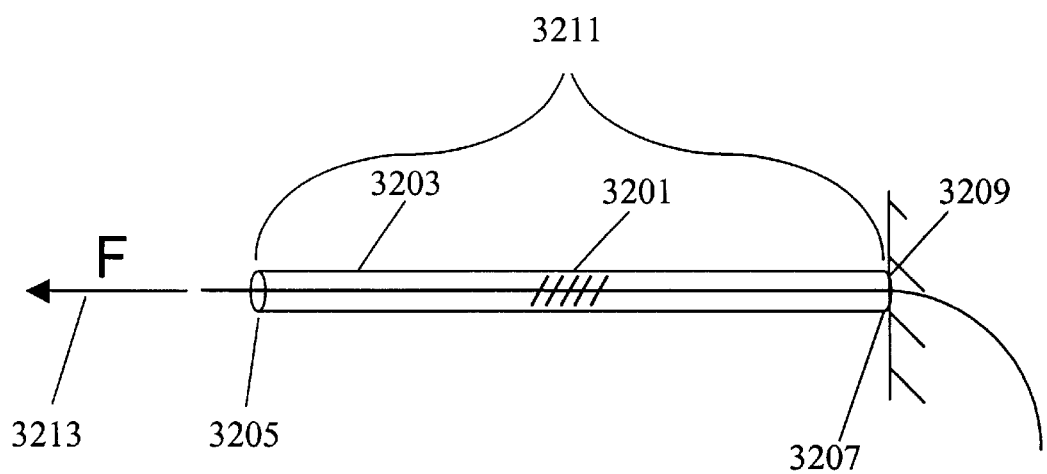
FIG. 34 is an illustration of a tunable grating filter employing a grating in a tube to control the amount of strain transferred to the grating for a given displacement and allowing for tuning in both directions if the fiber is pre-tensioned in the tube and the grating is stretched or relaxed.

FIG. 34 shows an extension to FIG. 33 where the fiber grating 3201 is placed into a tube 3203 and fixed at either end of the tube 3205, 3207. The tube is also fixed 3209. The length of the tube 3211 can be varied to control the length of the sensor that is being stretched by force F 3213 and thus control the amount of strain on the fiber for a given displacement controlled by a precision screw such as a micrometer or a picomotor such as the one available from New Focus. This configuration could be a tension only type of tunable filter similar to FIG. 33, or the fiber could be pre-strained in the tube to allow for a wavelength shift in both directions if the fiber was allowed to relax.

FIG. 35a and FIG. 35b show a tunable filter concept utilizing a diaphragm 3221 with a fiber grating attached onto or embedded into the diaphragm off of its neutral axis. With a pressure differential on the diaphragm 3223, 3225 the diaphragm will deflect up or down and put tension or compression on the fiber grating.

Figures 36A, 36B:
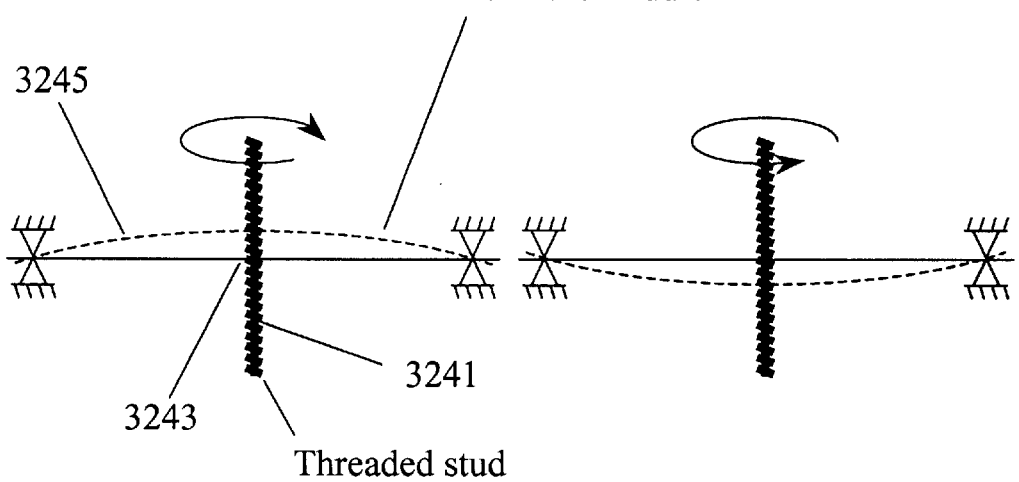
FIG. 36a and FIG. 36b are diagrams showing the deflection of a beam using a threaded stud to induce strain (positive or negative) in a grating.

FIG. 36a and FIG. 36b show an extension to the tunable filter concept shown in FIG. 30. In this case, a threaded stud 3241 is threaded through a tap 3243 in the beam 3245. As the stud 3241 is turned the beam 3245 is flexed up or down based on the direction of the turn.

Figure 37:
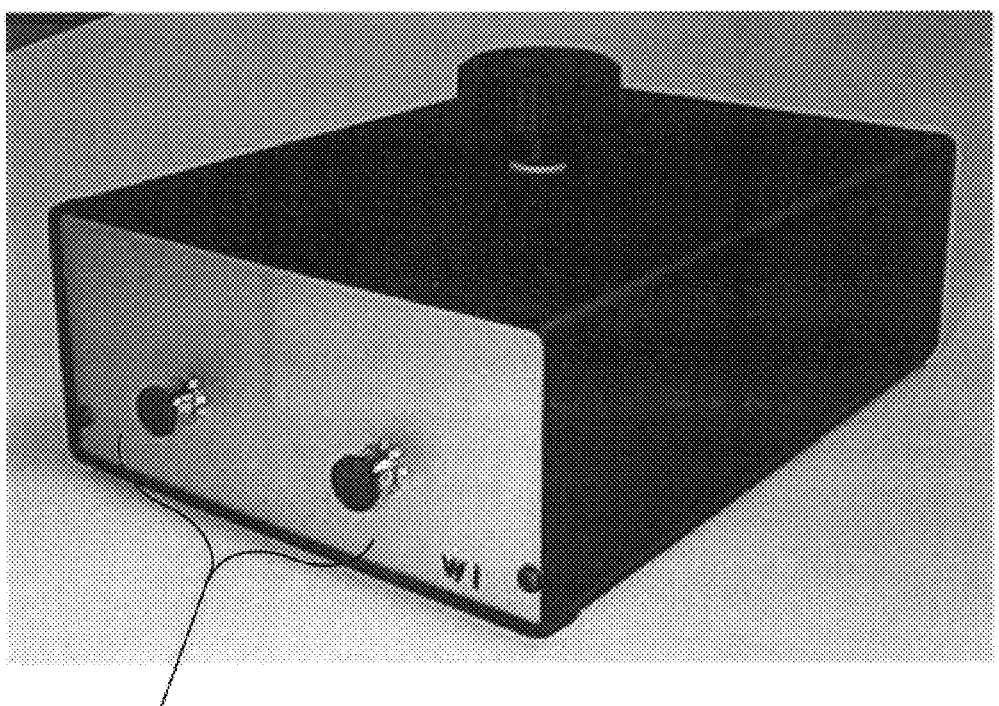
FIG. 37 is a photograph of the exterior of prototype with fiber optic connections and knob on top to turn a threaded stud and deflect a beam used to put tension and compression on the fiber grating.

FIG. 37 shows a picture of a prototype based on the concepts described in FIGS. 30 and 36. Here the tunable grating filter is enclosed in a box with an external knob to turn the threaded stud inside. The optical ports 3247 allow access to both sides of the grating to allow the filter to operate in transmission.

Figure 38:
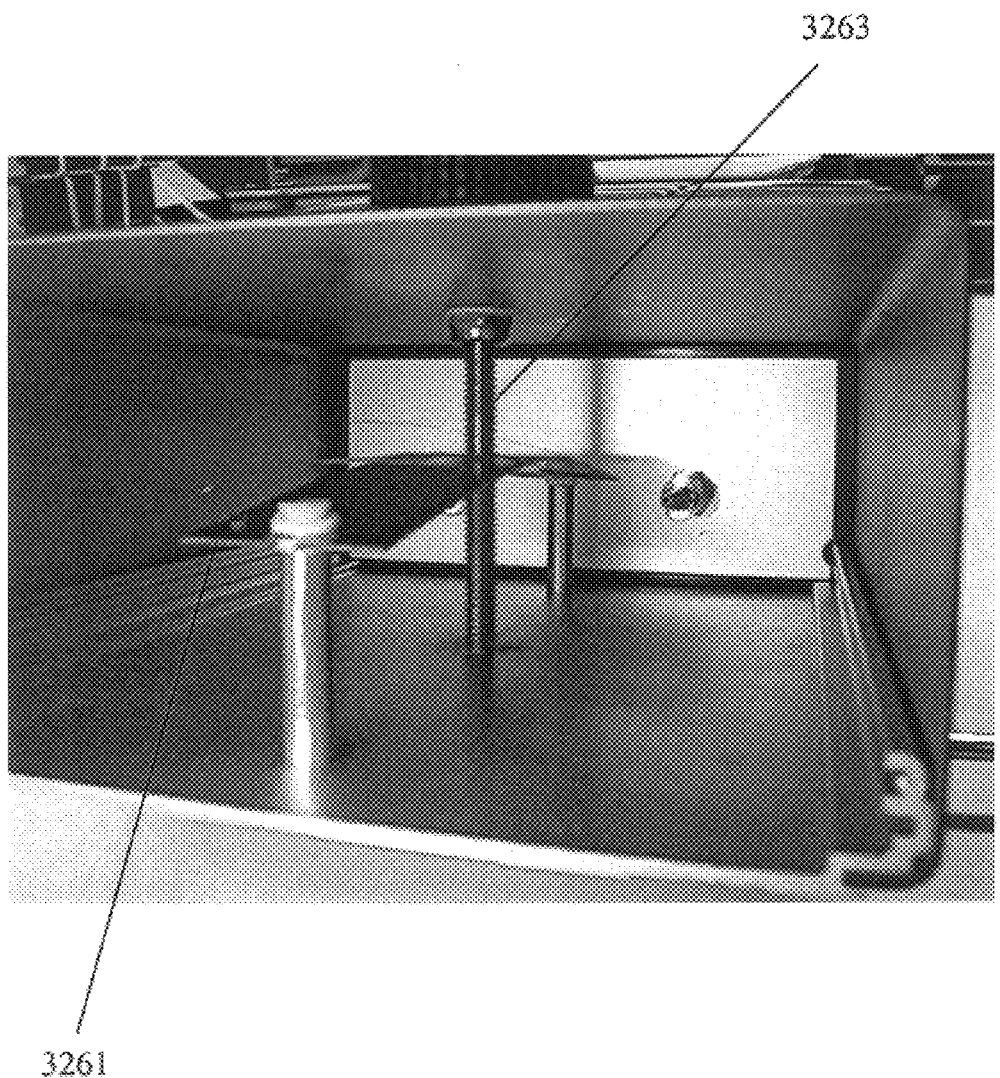
FIG. 38 is a photograph of the interior of prototype showing threaded stud, beam, and beam supports.

FIG. 38 shows a picture of the inside of the filter box of FIG. 37. Here the beam 3261 with the attached grating can be seen with the stud threaded 3263 through it.

Figure 39:
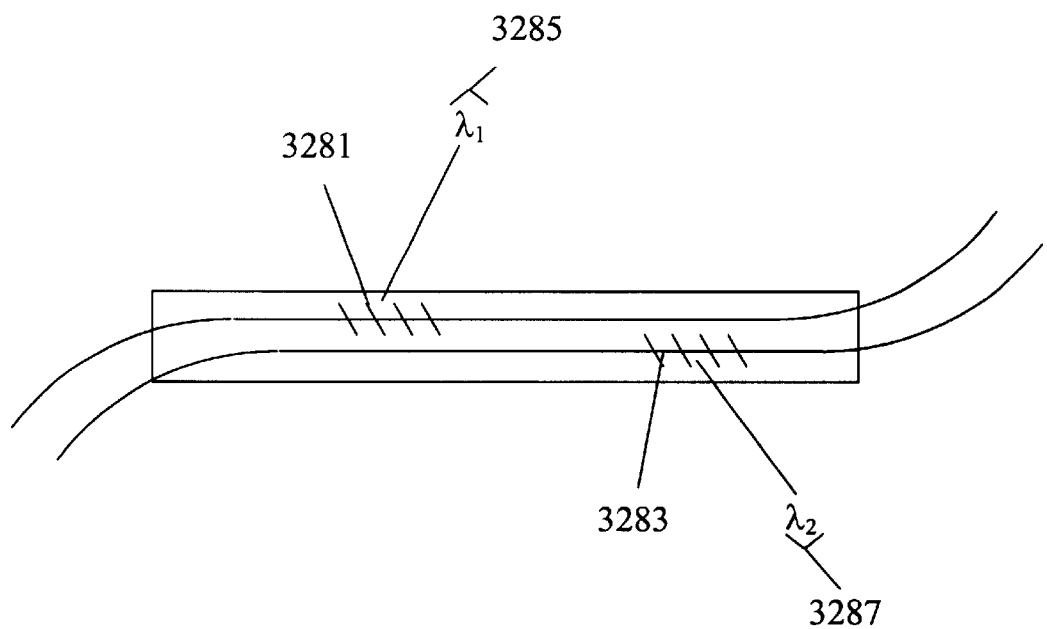
FIG. 39 is a diagram showing a beam with multiple color grating filters to filter different color grating sensors.

FIG. 39 shows an extension of the tunable filter concept where multiple gratings 3281,3283 of different wavelengths 3285,3287 are attached to or embedded into a beam with tuning provided by bending or a push/pull force. This allows for the potential of a single tunable filter handling multiple fiber grating sensors at different wavelengths.

Figure 40:
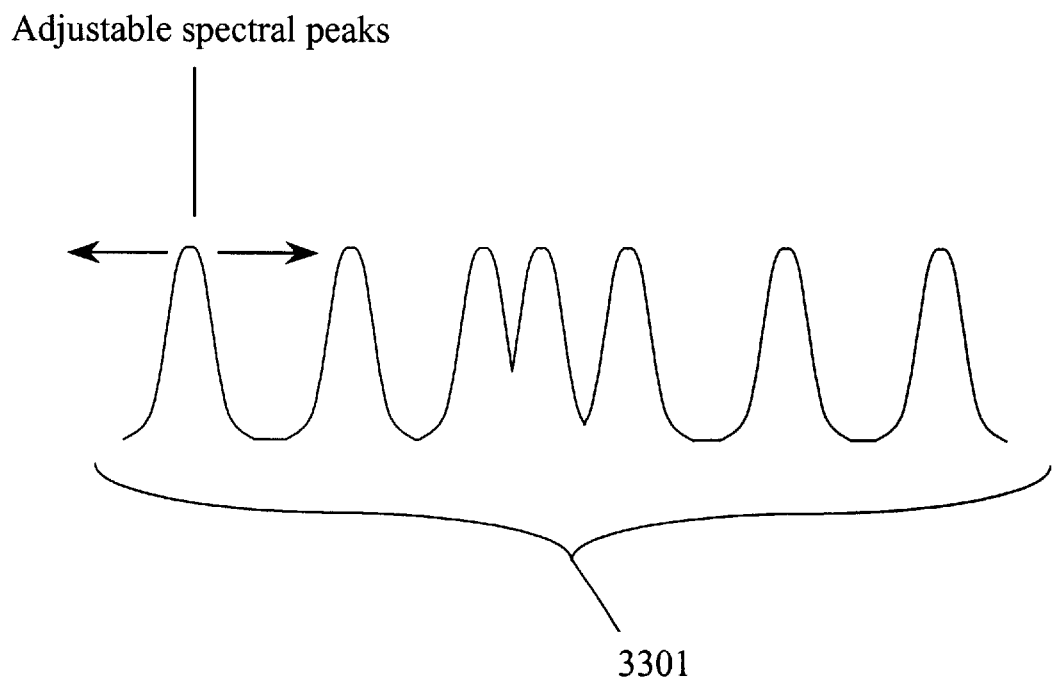
FIG. 40 is a diagram showing an adjustable comb filter.

FIG. 40 shows the spectral profile 3301 of a series of tunable gratings. If each spectral peak were tunable independently, then a comb filter could be formed.

Figure 41:
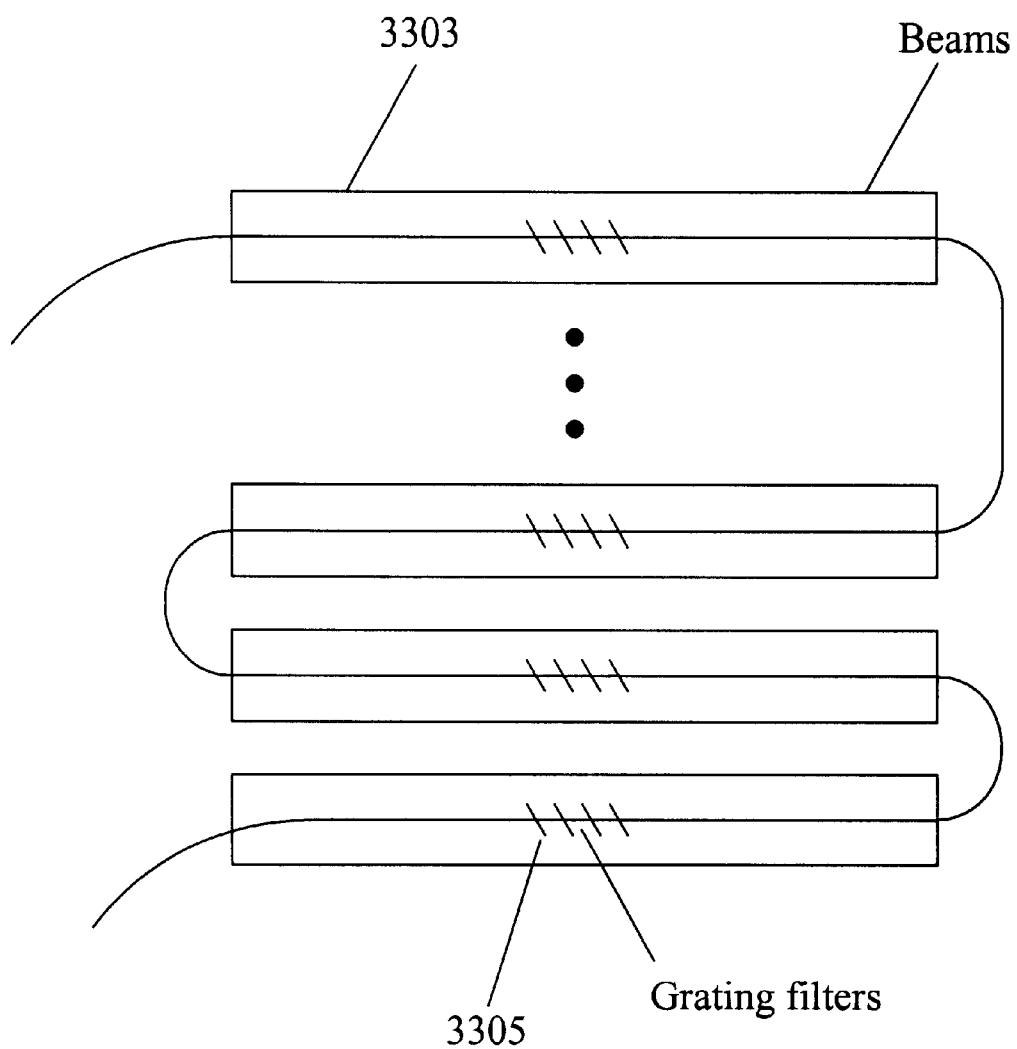
FIG. 41 is a diagram showing a series of beams with attached grating filters at different wavelengths to form an adjustable comb filter.

FIG. 41 shows a concept for the fiber grating comb filter shown in FIG. 40. A series of multiple beams 3303 or other tuning mechanisms each with a fiber grating 3305 of different wavelength attached or embedded could be connected together to form the comb filter.

Figure 42:
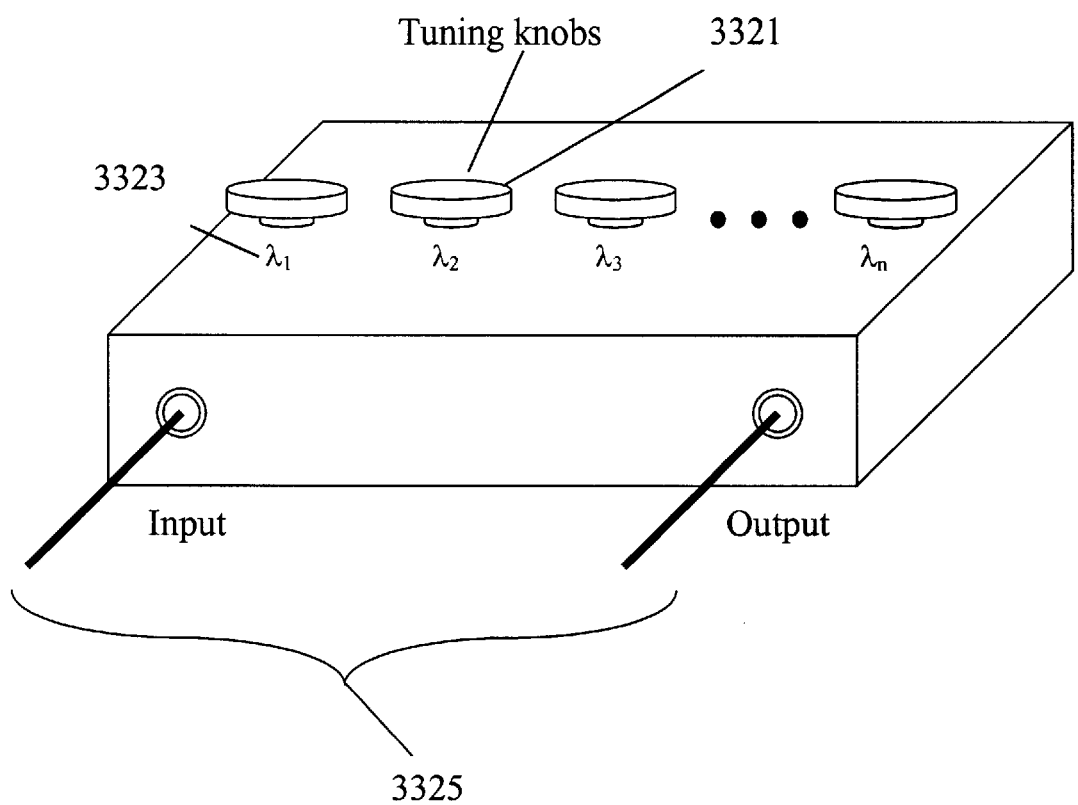
FIG. 42 is a diagram showing a configuration where adjusting each filter independently with a knob-beam configuration is possible.

FIG. 42 shows how the fiber grating comb filter could be packaged and tuned. A series of knobs 3321 connected to the beams with gratings at different wavelengths 3323 could be used to tune each individual grating to a higher or lower wavelength to form the desired comb profile. Optical ports 3325 would provide access to both ends of the series of gratings.

Figure 43:
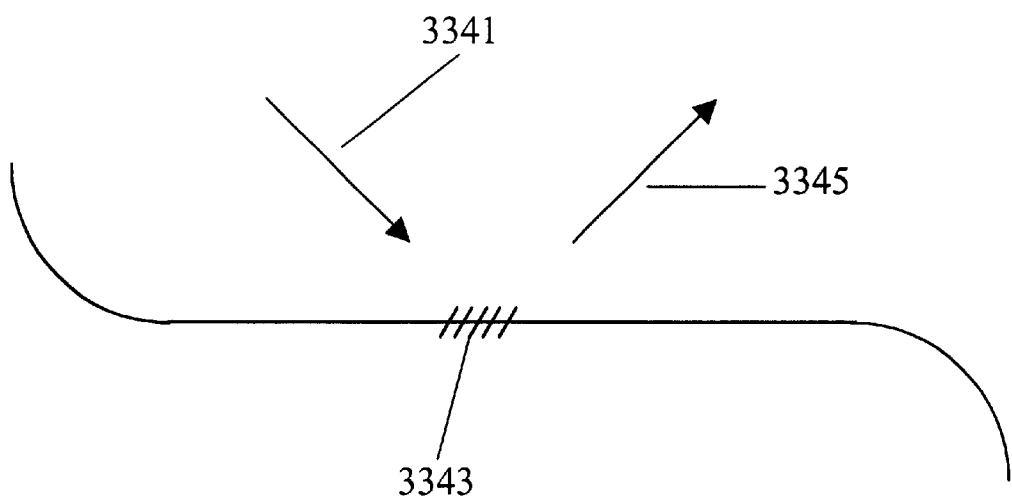
FIG. 43 is a diagram of a tunable grating filter based on thermal tuning.

FIG. 43 shows another concept for a tunable grating filter. As a fiber grating responds similarly to heat as it does to strain due to thermal expansion/contraction, a tunable filter based on heating/cooling the fiber grating is feasible. A heat input 3341 would shift the grating filter 3343 to a higher wavelength. A heat output 3345 or cooling would shift the grating filter to a lower wavelength.

In addition to a tunable grating filter to support higher sensitivity and multiplexing of the grating based sensor such as a chemical sensor, additional schemes are described below that further enhance the multiplexing potential of a fiber grating sensor system.

Figure 44:
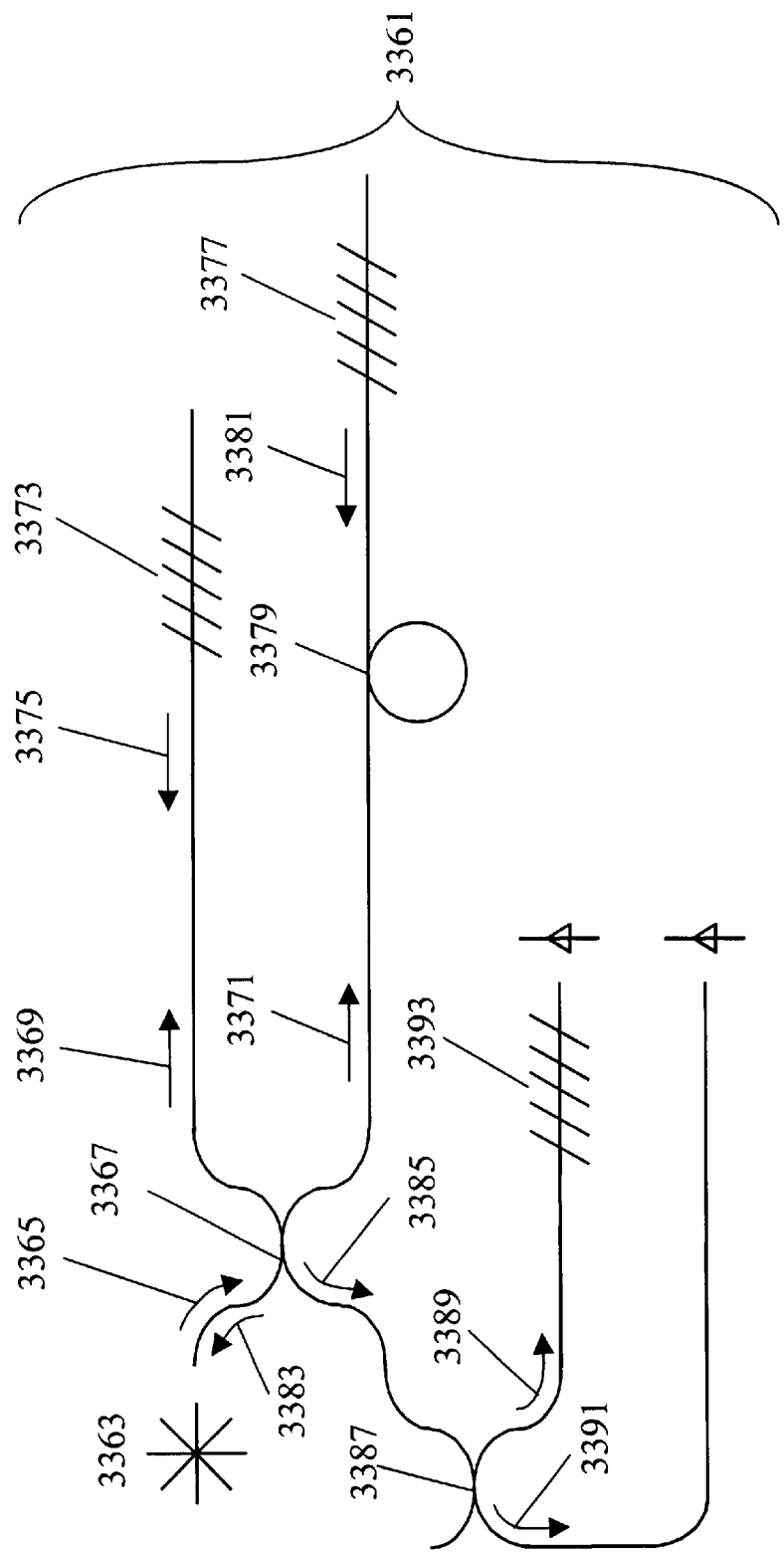
FIG. 44 is a diagram showing multiplexing of the high speed demodulation system by introducing a time delay.

FIG. 44 shows a modification of the demodulation system described in FIG. 27 where multiplexing is enabled through the use of time division multiplexing. The demodulation system 3361 consists of a pulsed broadband light source 3363 that directs a spectral pulse 3365 into a beam splitter 3367 and is split into two pulses 3369 and 3371. The pulse 3369 will arrive at the grating sensor 3373 first and a spectral peak 3375 will be reflected back. The spectral pulse 3371 will reach the grating sensor 3377 later due to a time delay 3379 that could consist of a coil of fiber. The grating sensor 3377 will then reflect a spectral peak 3381. The spectral peak 3375 will reach the beam splitter 3367 first and be split into two spectral peaks 3383 and 3385. Spectral peak 3383 will be directed back toward the light source 3363 and will have no effect. Spectral peak 3385 will be directed toward a second beam splitter 3387 that will split it into two spectral peaks 3389 and 3391. The spectral peak 3381 will reach the beam splitter 3367 after peak 3375 and will be split into two peaks that will follow the same paths as spectral peaks 3383 and 3385, only they will be delayed by the amount determined in the time delay 3379. This configuration allows for multiple gratings sensors at the same wavelength to be demodulated by one demodulation system with a single spectral filter 3393.

In some of the demodulation cases described above, only a single spectral peak being reflected from the grating sensor can be demodulated. The following figures describe methods for utilizing this same demodulation system for the case of gratings written onto birefringent fiber where there are multiple peaks per sensor, refer to U.S. Pat. Nos. 5,591,965 and 5,828,059.

Figure 45:
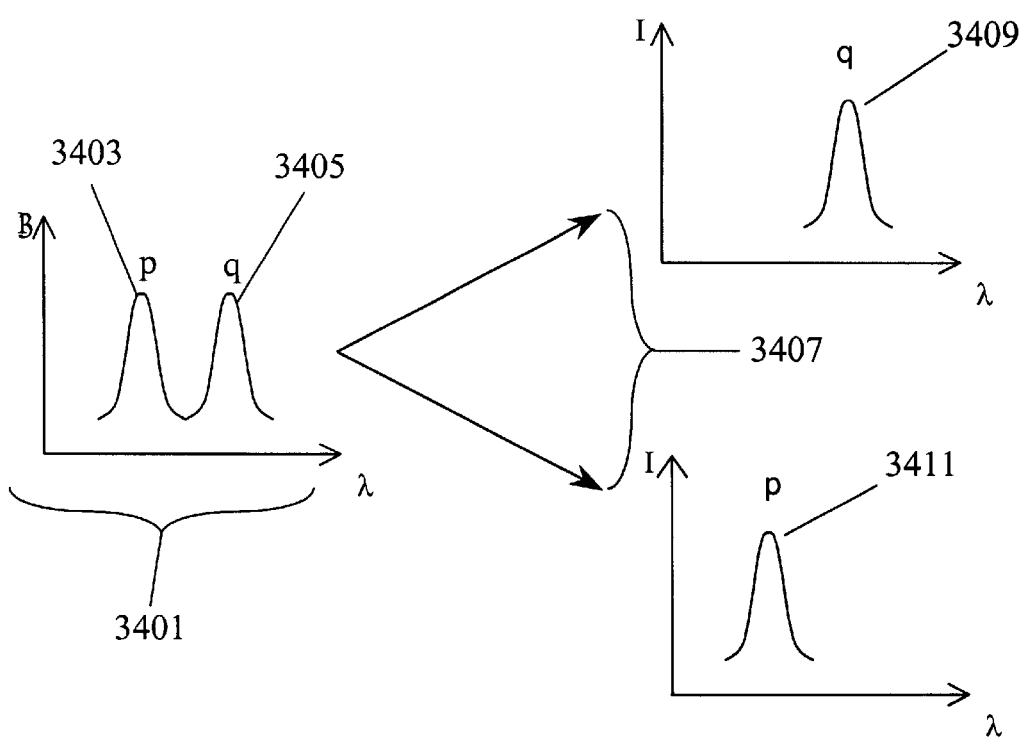
FIG. 45 is a diagram showing splitting the dual peak structure of a dual axis grating to two individual peaks.

FIG. 45 shows a typical spectral profile 3401 for a grating written onto birefringent fiber. The profile consists of two peaks 3403 and 3405 associated with the polarization states of the birefringent fiber onto which the grating is written. In order to utilize the above described high speed demodulation system, these polarization peaks 3403 and 3405 can be separated 3407 into two separate peaks 3409 and 3411 that are compatible with the high speed demodulation system.

Figure 46:
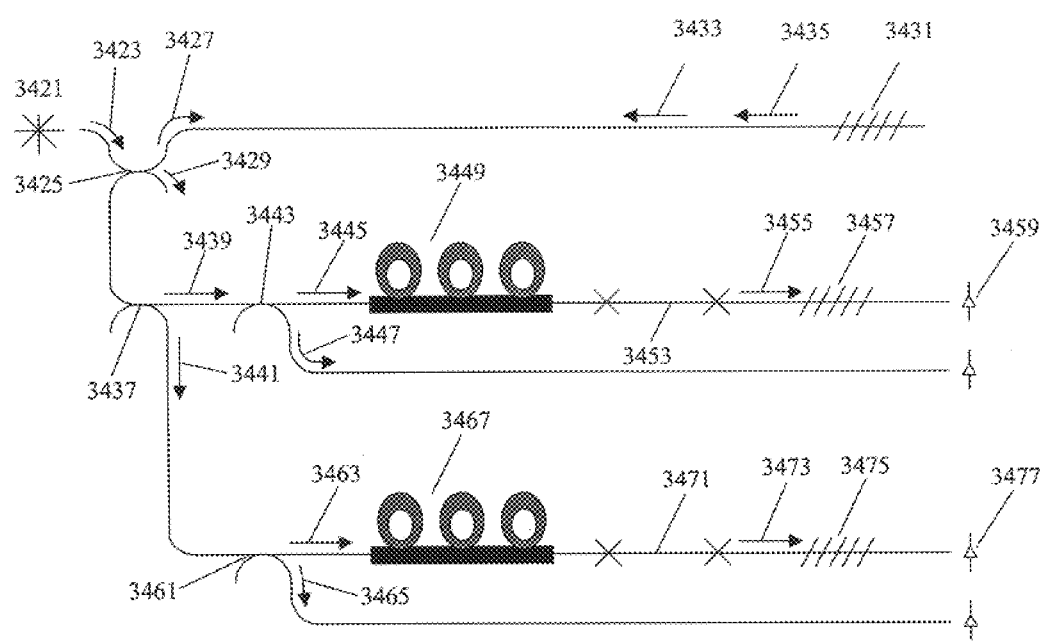
FIG. 46 is a diagram showing the use of polarization controllers to separate out the two polarization states associated with a dual axis(transverse) grating sensor.

FIG. 46 shows a demodulation system utilizing the concept of FIG. 45 to demodulate a grating written onto birefringent fiber with the demodulation system employing a spectral filter described previously. The broad band light source 3421 directs a broad band spectral profile 3423 into a beam splitter 3425 which splits the broad band profile 3423 into two broadband profiles 3427 and 3429. The profile 3429 can be dumped (ensuring no back reflections) or directed toward another grating sensor. The profile 3427 is directed toward a fiber grating sensor 3431 written onto birefringent fiber where two spectral peaks 3433 and 3435 associated with the polarization axes of the birefringent fiber will be reflected. These peaks are then directed toward the beam splitter 3425 and directed toward a second beam splitter 3437 and split into legs 3439 and 3441. The two peaks traveling along leg 3439 are directed into beam splitter 3443 and split into legs 3445 and 3447. The two peaks in leg 3445 are directed into a polarization controller 3449. A length of polarizing fiber 3453 is used to ensure that one of the polarization states is blocked. The peak single 3455 is then directed into a spectral filter 3457 and converted into an amplitude based measurement measurable by a detector 3459 as described in FIG. 27. The leg 3447 provides the reference leg described in FIG. 27. The leg 3441 directs the two peaks associated with the two polarization states into a beam splitter 3461 that splits into two legs 3463 and 3465. Leg 3463 directs the two peaks into a polarization controller 3467. A length of polarizing fiber 3471 is used to ensure that one of the peaks is blocked. The peak 3473 is then directed into a spectral filter 3475 and converted into an amplitude based measurement measurable by a detector 3477 as described in FIG. 27. The leg 3465 provides the reference leg described in FIG. 27. To ensure that the polarization controllers and polarizing fibers are blocking the correct polarization peaks, a simple calibration could be performed by loading the fiber grating in transverse and noting whether or not the signals on the respective detectors change as expected.

Figure 47:
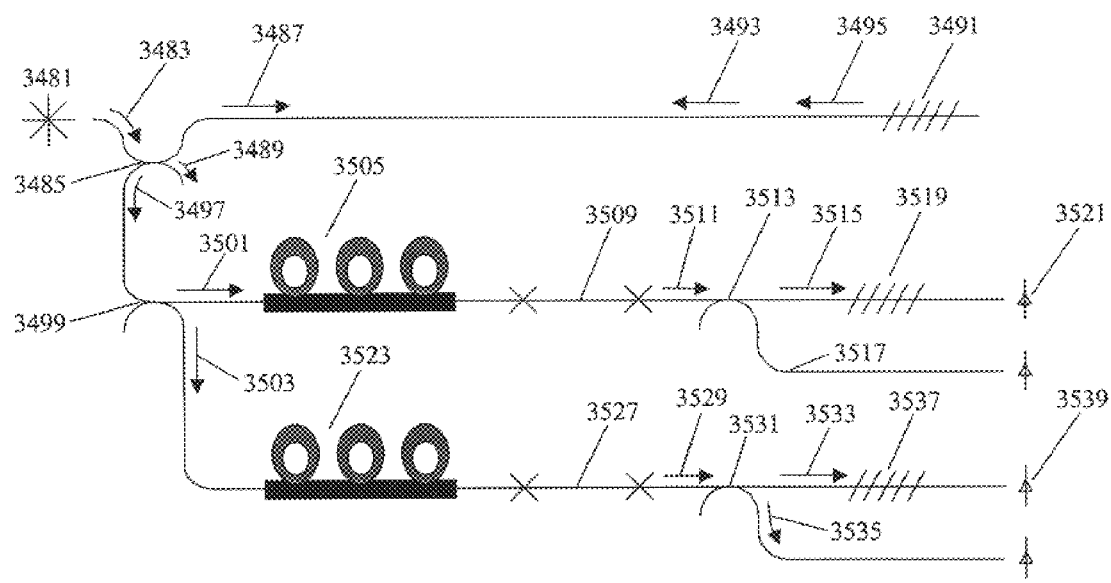
FIG. 47 is a diagram of an alternative design where the polarization controllers and polarizing fiber are placed before the last beam splitters to reduce errors associated with inconsistent polarization states in the filtered and reference legs.

FIG. 47 shows another method to separate the polarization states of the grating written onto birefringent fiber. This method places the polarization controllers before the beam splitter that splits the spectral data between the filtered and reference leg reducing errors associated with inconsistent polarization states in the filtered and referenced legs. A broadband light source 3481 outputs a broadband profile 3483 to a beam splitter 3485 that splits the profile 3483 into two legs 3487 and 3489. The leg 3489 is dumped or can be connected to another grating sensor. The leg 3487 guides the broadband light to a fiber grating sensor 3491 that consists of a grating written onto birefringent fiber that reflects two spectral peaks 3493 and 3495 each associated with a polarization state of the birefringent fiber. These peaks 3493 and 3495 are then directed to the beam splitter 3485 and directed 3497 into a beam splitter 3499 that splits into legs 3501 and 3503. The two peaks in leg 3501 are directed into a polarization controller. Polarizing fiber 3509 ensures that one of the polarization states is dropped. The peak 3511 is then directed in to a beam splitter 3513 that splits into two legs 3515 and 3517. Leg 3515 directs the single peak associated with one of the polarization states of the fiber grating sensor written onto birefringent fiber into a spectral filter 3519 that converts the spectral information into an amplitude based signal measurable by a detector 3521. The leg 3517 provides the reference leg. The two peaks in leg 3503 are directed into a polarization controller 3523. A length of polarizing fiber 3527 ensures that one of the polarizing states is dropped. The peak 3529 is then directed into a beam splitter 3531 that splits into two legs 3533 and 3535. Leg 3533 directs the single peak associated with one of the polarization states of the fiber grating sensor written onto birefringent fiber into a spectral filter 3537 that converts the spectral information into an amplitude based signal measurable by a detector 3539. The leg 3535 provides the reference leg.

Figure 48:
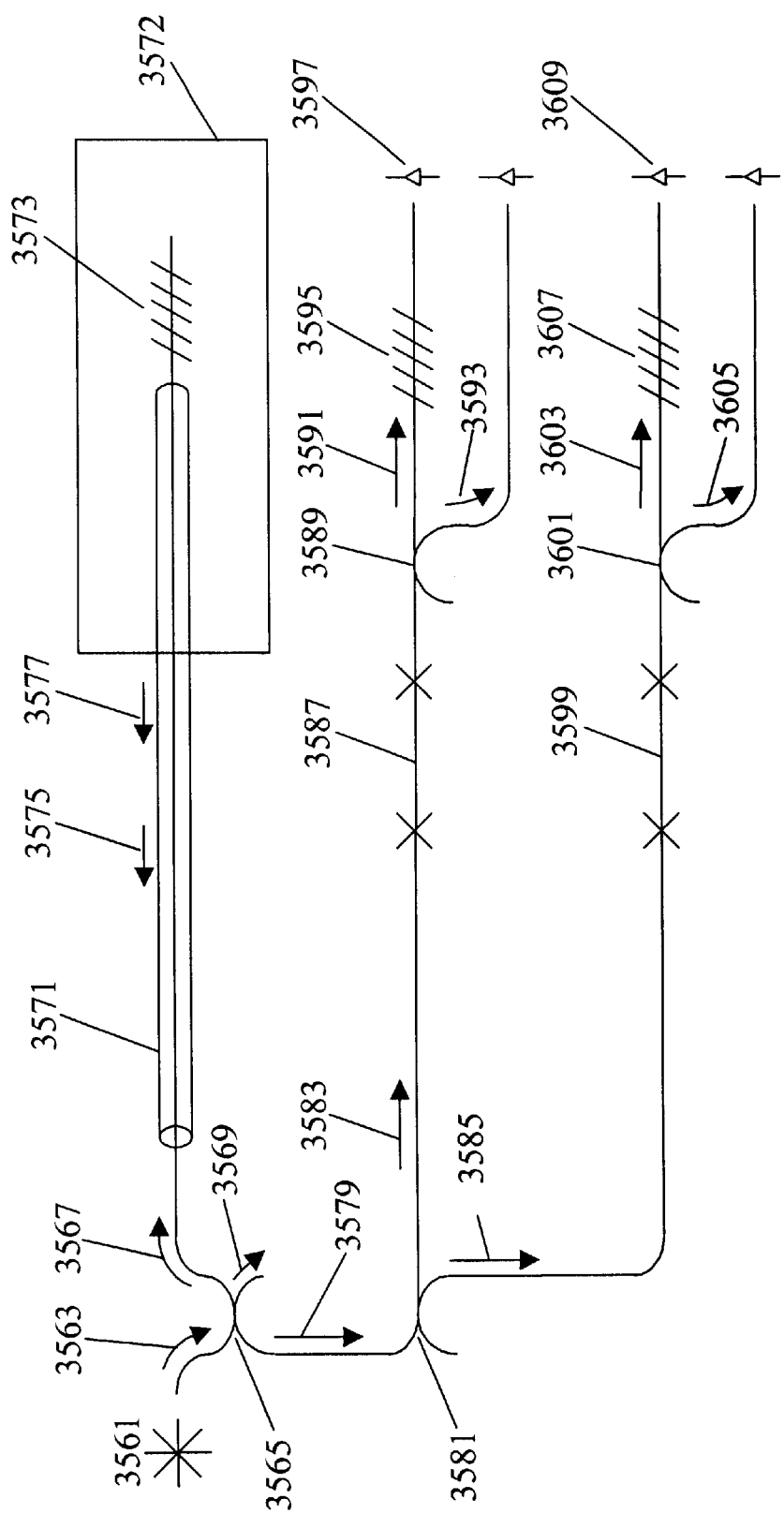
FIG. 48 is a diagram showing the use of polarization maintaining (PM) fiber and beam splitters in conjunction with polarizers to control polarization states.

FIG. 48 shows an alternative system where polarization maintaining fiber is used throughout most of the system along with polarization maintaining beam splitters so that the two polarization states are each directed to the appropriate demodulator filter set. A broad band light source 3561 directs broad band light 3563 into a polarization maintaining beam splitter 3565 that splits the broadband light 3563 into two parts 3567 and 3569. Broadband light 3569 is dumped or can be connected to another fiber grating sensor. Broadband light 3567 is directed along the fiber that is placed into a tube 3571 that provides strain relief for the fiber going into a part 3572 to a fiber grating sensor 3573 written onto birefringent fiber that reflects two peaks 3575 and 3577 associated with each polarization state of the birefringent fiber. The peaks 3575 and 3577 are directed to beam splitter 3565 and then directed to polarization maintaining beam splitter 3581 that splits into two legs 3583 and 3585. The leg 3583 directs both peaks associated with the polarization axes of the fiber grating written onto birefringent fiber to a length of polarizing fiber 3587 that is oriented to block one of the polarization states. The fiber and beam splitters after this length of polarizing fiber 3587 does not need to be polarization maintaining. The resulting single peak from 3587 then travels to a beam splitter 3589 and is split into legs 3591 and 3593. Leg 3591 directs the single peak to a fiber grating filter 3595 that converts the spectral information into an amplitude based signal measurable by a detector 3597. The 3593 leg forms the reference leg. The leg 3585 directs both peaks associated with the polarization axes of the fiber rating written onto birefringent fiber to a length of polarizing fiber 3599 that is oriented to block one of the polarization states different from that of 3587. The fiber and beam splitters after this length of polarizing fiber 3599 does not need to be polarization maintaining. The resulting single peak from 3599 then travels to a beam splitter 3601 and is split into legs 3603 and 3605. Leg 3603 directs the single peak to a fiber grating filter 3607 that converts the spectral information into an amplitude based signal measurable by a detector 3609. The 3605 leg forms the reference leg.

Figure 49:
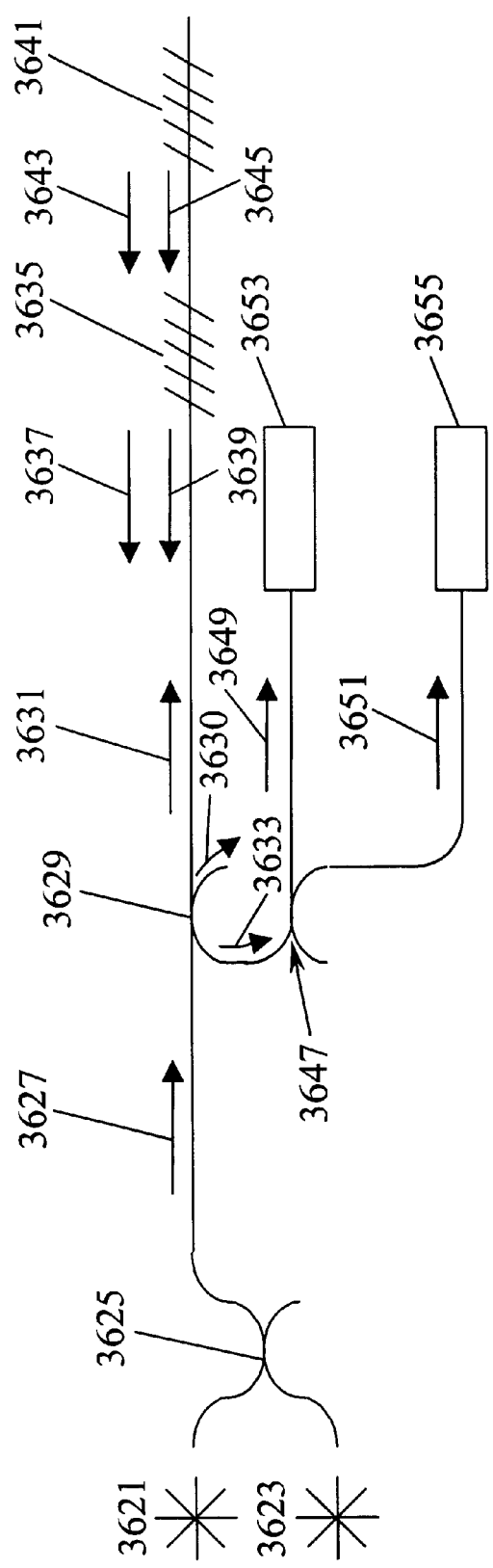
FIG. 49 is a diagram showing multiplexing of the transverse gratings by combining two light sources and splitting each wavelength to separate demodulators.

FIG. 49 shows a method to add multiplexing capability to the system shown in FIG. 48 by employing two broadband light sources and two gratings written at different wavelengths. In this case, two broadband light sources 3621 and 3623 of different central wavelengths are combined using a wavelength division multiplexer 3625. The resulting two broadband profiles are directed into leg 3627 and to a beam splitter 3629 that splits into two legs 3631 and 3630. Leg 3630 is dumped or could be connected to a fiber grating sensor. Leg 3631 directs the two broadband profiles to a grating sensor 3635 written onto birefringent fiber and reflecting two peaks 3637 and 3639 each associated with the polarization axes of the birefringent fiber. The throughput of the grating sensor 3635 is directed to another grating sensor 3641 written onto birefringent fiber at a different wavelength than grating sensor 3635 and reflecting two peaks 3643 and 3645 each associated with the polarization axes of the birefringent fiber. The resulting four peaks 3637, 3639, 3643, and 3645 are then directed to a beam splitter 3629 and directed to a wavelength division multiplexer (providing lower loss)or a beamsplitter 3647 that divides the four peaks into two pairs associated with the center wavelengths of the broadband light sources 3621 and 3623. One pair of peaks travels along leg 3649 into a demodulation system 3653 similar to that described in FIG. 48. The other pair of peaks travels along leg 3651 into a demodulation system 3655 similar to that described in FIG. 48. The approach of FIG. 49 could be extended to large numbers of sensors by using the wavelength division multiplexing element 3647 to divide the spectrum into discrete packets for each fiber grating sensor, demodulation subsystem combination.

In order to multiplex a large number of fiber grating sensors using wavelength division multiplexing while retaining high speed characteristics and sensitivity it would be highly desirable to have the lowest possible loss system available.

Figure 50:
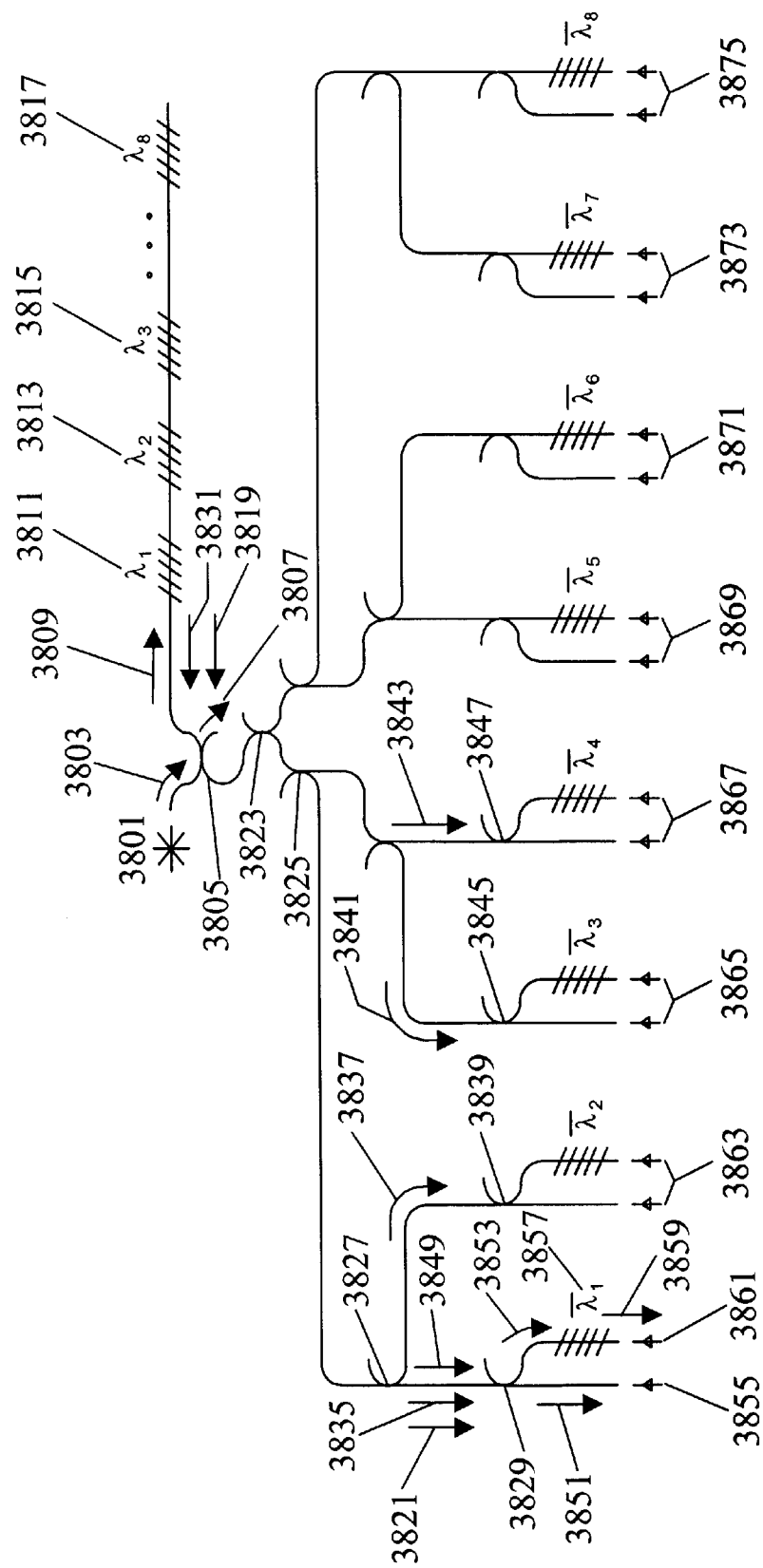
FIG. 50 is a diagram showing a "Cascading" configuration where beam splitters are used to divide the reflected light from the sensors among the separate demodulators.

FIG. 50 shows a system that may be used to multiplex fiber optic gratings at high speed using low cost 2 by 2 fiber couplers. There are different means to operate the system shown in FIG. 50. As an example the light source 3801 could be a broadband light source such as a light emitting, super-radiant laser diode or doped fiber light source (erbium doped light sources being currently most common), which could be used to illuminate a series of fiber grating sensors spaced in wavelength simultaneously. The light source 3801 could also be a tunable light source such as a tunable laser diode that could be used to spectrally scan the string of fiber grating sensors. Returning to FIG. 50, the light source 3801 emits a beam of light that is coupled into one end of the fiber coupler 3805 (bulk optic components or integrated optic beamsplitters could be used, currently the losses associated with these devices are higher and they are not as cost effective). The light beam 3803 is then split by the beam-splitter 3805 into a light beam 3807 that exits the system in FIG. 50 but it could also be used to illuminate another set of fiber grating sensors on a second fiber line. The second split portion of the light beam 3803 is the light beam 3809 that is directed toward the fiber grating sensor 3811 centered about the wavelength $\lambda_1$. A portion 3819 of the light beam 3809 is reflected by the fiber grating sensor 3811. The spectral change of the light beam 3819 is indicative of the environmental state of the fiber grating. The light beam 3819 then traverses the fiber beamsplitter 3805 a second time and a portion of it is directed to the beamsplitter 3823 where it is split again by the beamsplitters 3825 and 3827 eventually resulting in the light beam 3821 hitting the beamsplitter 3829. The light beam 3809 then proceeds past 3811 to the fiber grating sensor 3813 that is centered about the wavelength $\lambda_2$. A portion 3831 of the light beam 3809 is reflected off the fiber grating sensor 3813 and is split by the beam-splitters 3805, 3823, 3825 and 3827 to form the light beam 3835 that is directed toward the beamsplitter 3829. In a similar manner portions of the light beam 3809 are reflected from the fiber grating sensors 3815 centered about $\lambda_3$ and 3817 centered about $\lambda_8$. The net result is that at the beam-splitter 3829 there is a light beam consisting of reflections off the series of fiber grating sensors 3811, 3813, 3815 and 3817 divided by the action of the beamsplitters 3805, 3823, 3825 and 3827. A similar light beam 3837 falls onto the beamsplitter 3839. Analogous combination light beams 3841 and 3843 fall onto the beamsplitters 3845 and 3847 respectively.

When the light beam 3849 corresponding to reflections off all the fiber grating sensors 3811, 3813, 3815 . . . 3817 falls onto the beamsplitter 3829 it splits into the light beams 3851 and 3853. The light beam 3851 falls onto the output detector 3855 whose output signal acts as reference. The light beam 3853 passes through the fiber grating filter 3857 that acts to modulate the spectral signal reflected from the fiber grating sensor 3811. The light beam 3859 passing through the fiber grating filter 3857 then falls onto the output signal detector 3861. Note that the output signal from detector 3861 contains a constant component associated with the reflections off all the other fiber grating sensors in the system in addition to that of 3811. The result is an offset for the output signal that becomes increasingly large with additional fiber grating sensors. Similar considerations apply to the beamsplitter, fiber grating filter detector sets 3863, 3865, 3867, 3869, 3871, 3873 and 3875.

Another approach to the fiber grating sensor system shown in FIG. 50 is to have the light source 3801 be a tunable laser. In this case each fiber grating sensor 3811, 3813, 3815, . . . 3817 is illuminated in sequence. The only variation in intensity as the light source is swept corresponds to the filter/detector pair corresponding to the illuminated grating. As an example when fiber grating sensor 3811 is swept the reflected light beam from 3811 is directed through the series of beamsplitters 3805, 3823, 3825, 3827 and 3829 to the fiber grating filter 3857 which in turn modulates the swept signal and by comparing the output of 3861 to 3855 the wavelength may be determined. Similarly the output of the fiber sensor grating 3813 can be read out by the optics/detector set 3857, fiber sensor grating 3815 by the optics/detector set 3865 and 3817 by the optics/detector set 3875. While one fiber sensor grating is being readout by the tunable laser 3801 the other optics/detector sets have a fixed ratio.

Figure 51:
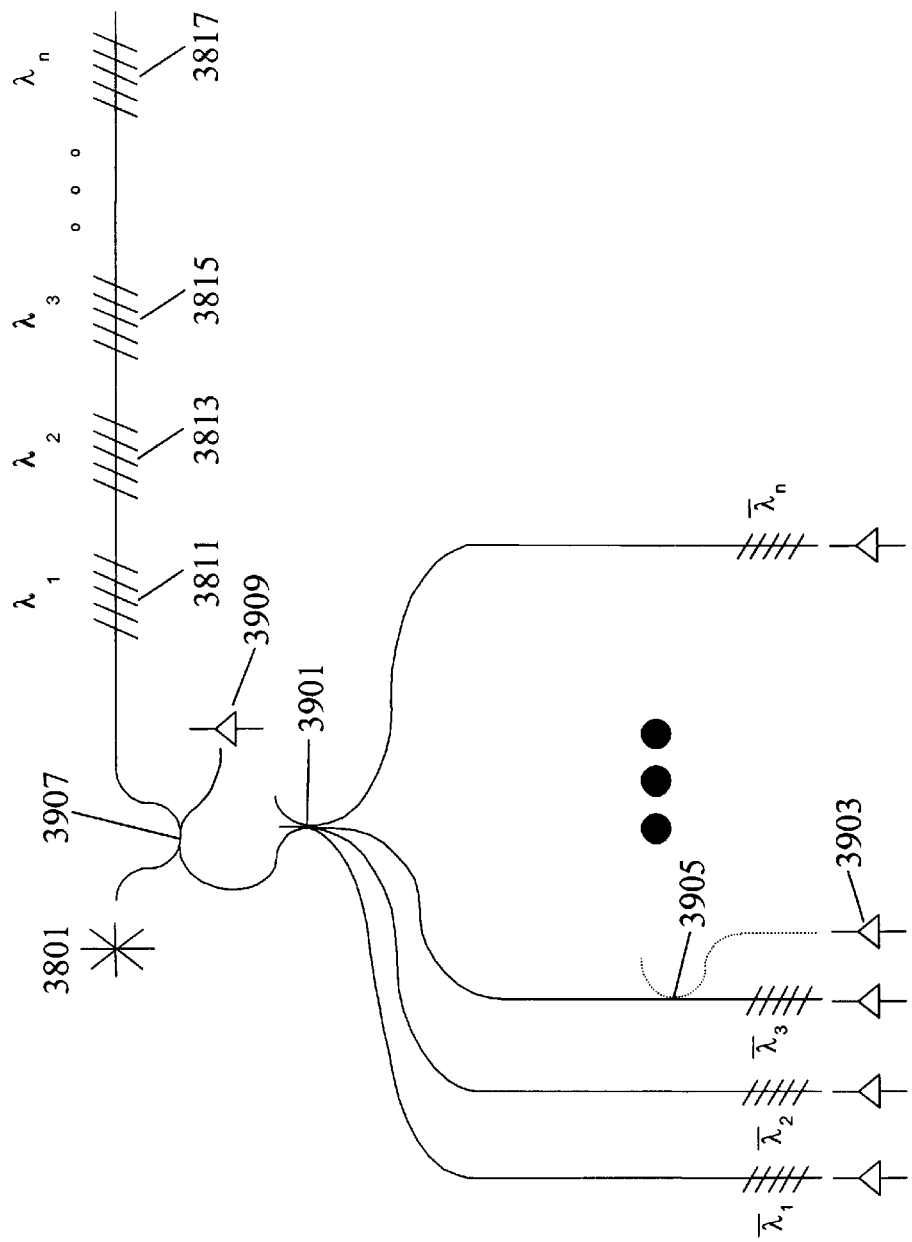
FIG. 51 is a diagram showing the alternate location of detectors.

FIG. 50 illustrates the case where two by two couplers are used. As shown in FIG. 51 it is also possible to use 1 by n couplers to achieve similar results. In this case the same light source 3801 is used to illuminate the sequence of fiber grating sensors 3811, 3813, 3815 and 3817. The reflected light beams from these fiber grating sensors are then directed to the 1 by n beamsplitter 3901 into n light beams each of which is directed through a fiber grating filter and onto the output detectors corresponding to each fiber grating sensor. In the simplest case the spectral signal would be modulated directly and not referenced. Reference detectors such as 3903 could be added with reference beamsplitters such as 3905 to compensate for system level fluctuations. An alternative configuration would be to place a reference detector 3909 at one of the output legs of the two by two beamsplitter 3907.

Figure 52:
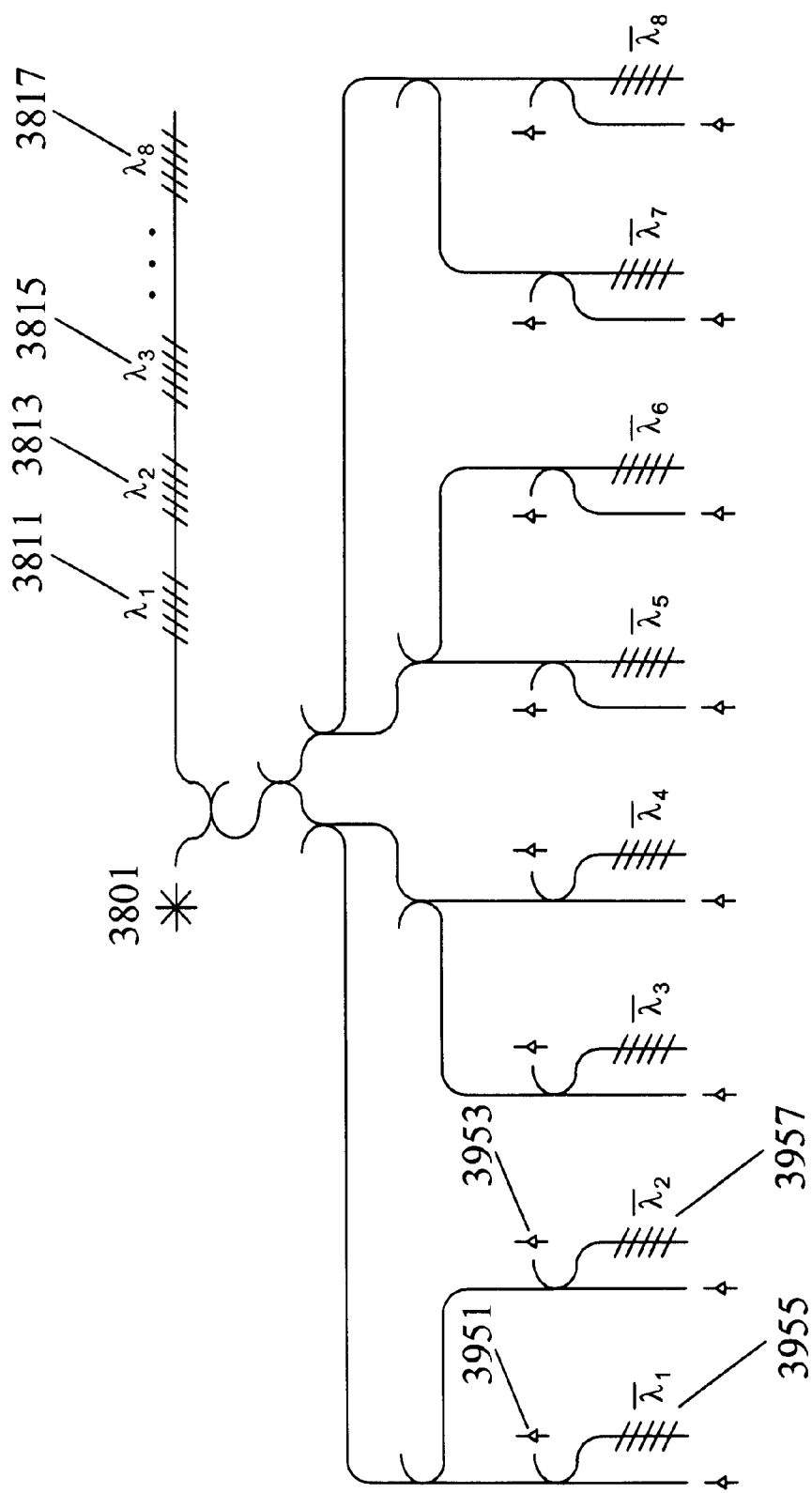
FIG. 52 is a diagram showing another alternate location of detectors to eliminate background light levels compared to FIG. 50.

FIG. 52 shows a configuration of a multiplexed fiber grating sensor system similar to that shown in FIG. 50 where instead of the output signal detectors monitoring the optical beams passing through the filters the light is reflected. This configuration eliminates cross talk between the fiber gratings. As an example the reflection from the fiber grating sensor 3811 is modulated only by the fiber grating filter 3955 which is designed to modulate light only about the center frequency of the fiber grating sensor 3811. The modulated light is then reflected to the output detector 3951. In a similar manner the fiber grating filter 3957 acts only to modulate the reflected light from the fiber grating sensor 3813 and in turn directs its modulated output light signal to the detector 3953. The configuration in FIG. 49 could be modified to replace the two by two couplers with a 1 by n coupler in direct analogy to FIG. 51.

Figure 53:
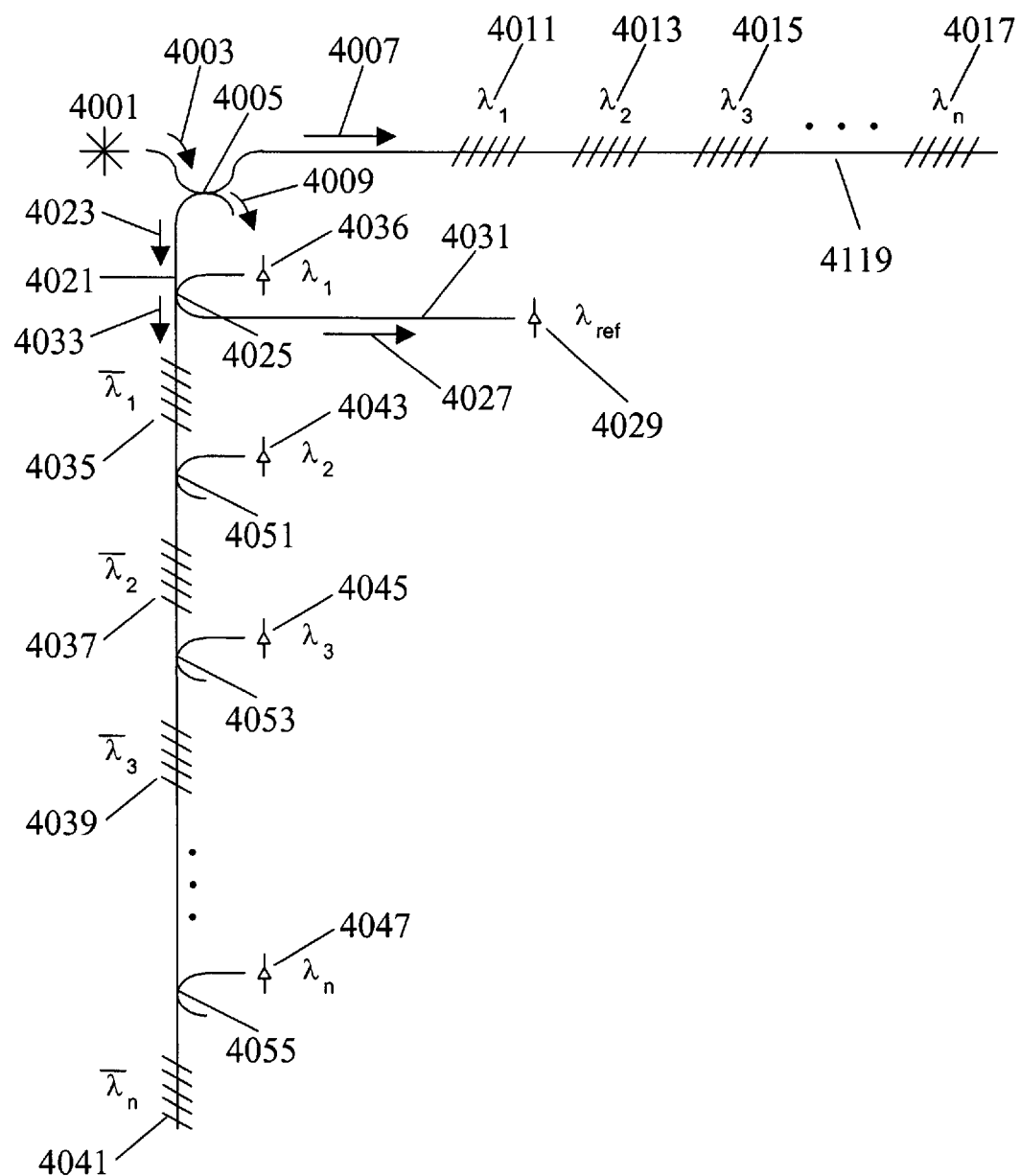
FIG. 53 is a diagram showing another method to demodulate several in line fiber grating sensors. This system also provides the capability of an absolute measurement by providing a reference detector.

FIG. 53 illustrates a system comprised of fiber gratings in a single fiber line with a series of fiber beamsplitters. This system can be operated in a number of different ways. In the first case consider the light source 4001 to be a broadband light source that might be a light emitting diode or a superradiant diode. The light source 4001 couples the light beam 4003 into the beamsplitter 4005. A portion of the light beam 4007 is directed through a series of fiber gratings 4011, 4013, 4015 . . . 4017 in the optical fiber line 4119. Another portion of the beam 4003 that is split by the beamsplitter 4005 is split off into the light beam 4009 that exits the system in FIG. 53 but alternatively could be used to support another line of fiber gratings. The reflected spectra from the fiber gratings 4011, 4013, 4015 . . . 4017 return to the beamsplitter 4005 and a portion of these spectra are directed along the output fiber 4021 as the light beam 4023. The light beam 4023 passes to the first fiber beamsplitter 4025 and a portion of it 4027 is split off to the reference detector 4029 along the fiber 4031. The signal from the detector 4029 is used to monitor the overall light level of the light source and components up to this point in the system. The second portion of the beam 4023, 4033 is directed to the fiber grating filter 4035 that has a wavelength designed to match that of fiber grating sensor 4011. The reflected spectra from the fiber grating filter 4035 is then directed back to the beamsplitter 4025 and onto the detector 4036. In a similar manner reflections from the fiber grating filters 4037, 4039 and 4041 are directed to the detectors 4043, 4045 and 4047. Note that the first detector 4036 response includes signals that include reflections from all the filters 4035, 4037, 4039 and 4041. These reflections are reduced in intensity through the action of the beamsplitters 4025, 4051, 4053 and 4055. Since there are n signals from the n fiber grating spectra reflected by the filters 4035, 4037, 4039 and 4041 that are directed to the output detectors 4036, 4043, 4045 and 4047 a system of equations is established that can be used to separate the signals for each individual sensor 4011, 4013, 4015 and 4017. The reference detector 4029 can be used to establish a baseline to compensate for light source 4001 and system level fluctuations before the string of fiber grating filters 4035, 4037, 4039 and 4041.

A second means to operate the system of FIG. 53 is to have the light source 4001 be tunable over the range of the fiber grating sensors 4011, 4013, 4015 and 4017. In this case as the light source is tuned over fiber grating 4011 a reflection off this grating reflects off the filter 4035. A portion of the reflected signal is directed to the output detector 4029 that can be referenced against the output monitoring detector 4037. In a similar manner fiber grating sensor 4013 can be monitored via fiber grating filter 4037 using the output detector 4043. Fiber grating sensor 4015 can be monitored via fiber grating filter 4039 and output detector 4045. Fiber grating sensor 4017 can be monitored via fiber grating filter 4041 and output detector 4047. Since only one fiber grating is illuminated at a time the signals on the output detectors 4036, 4043, 4045 and 4047 are not mixed and it is not necessary to solve a series of equations. The limitations of this approach rather than the first one described in association with FIG. 53 involve the speed with which the light source may be tuned limiting the overall response of the system and the cost of the tunable light source relative to a broadband one such as a light emitting diode.

Figure 54:
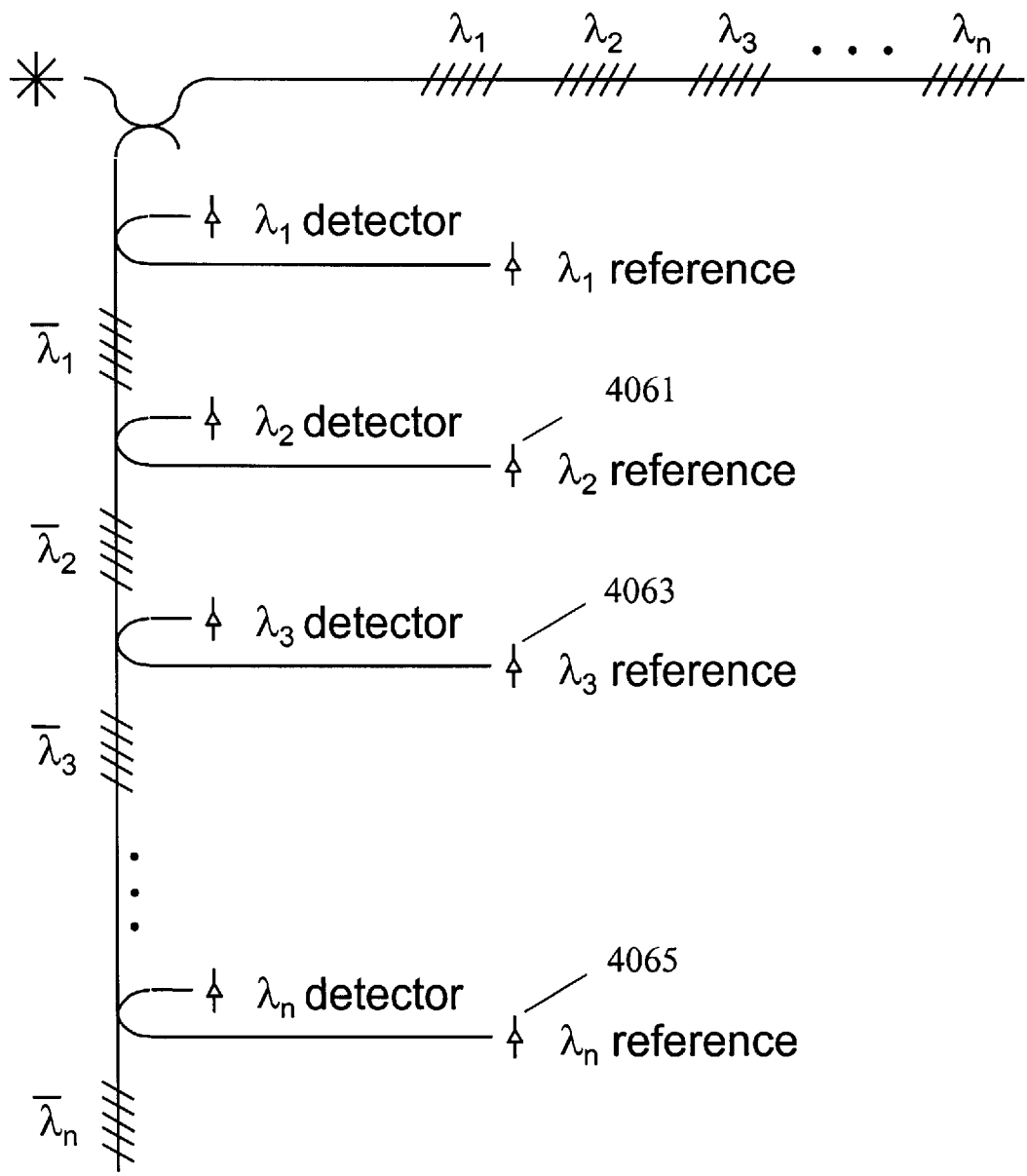
FIG. 54 is a diagram showing an alternate configuration with reference detectors on each leg.

FIG. 54 is similar to FIG. 53 with the addition of the reference detectors 4061, 4063 and 4065 to aid in eliminating errors due to component induced intensity fluctuations in the system.

Figure 55:
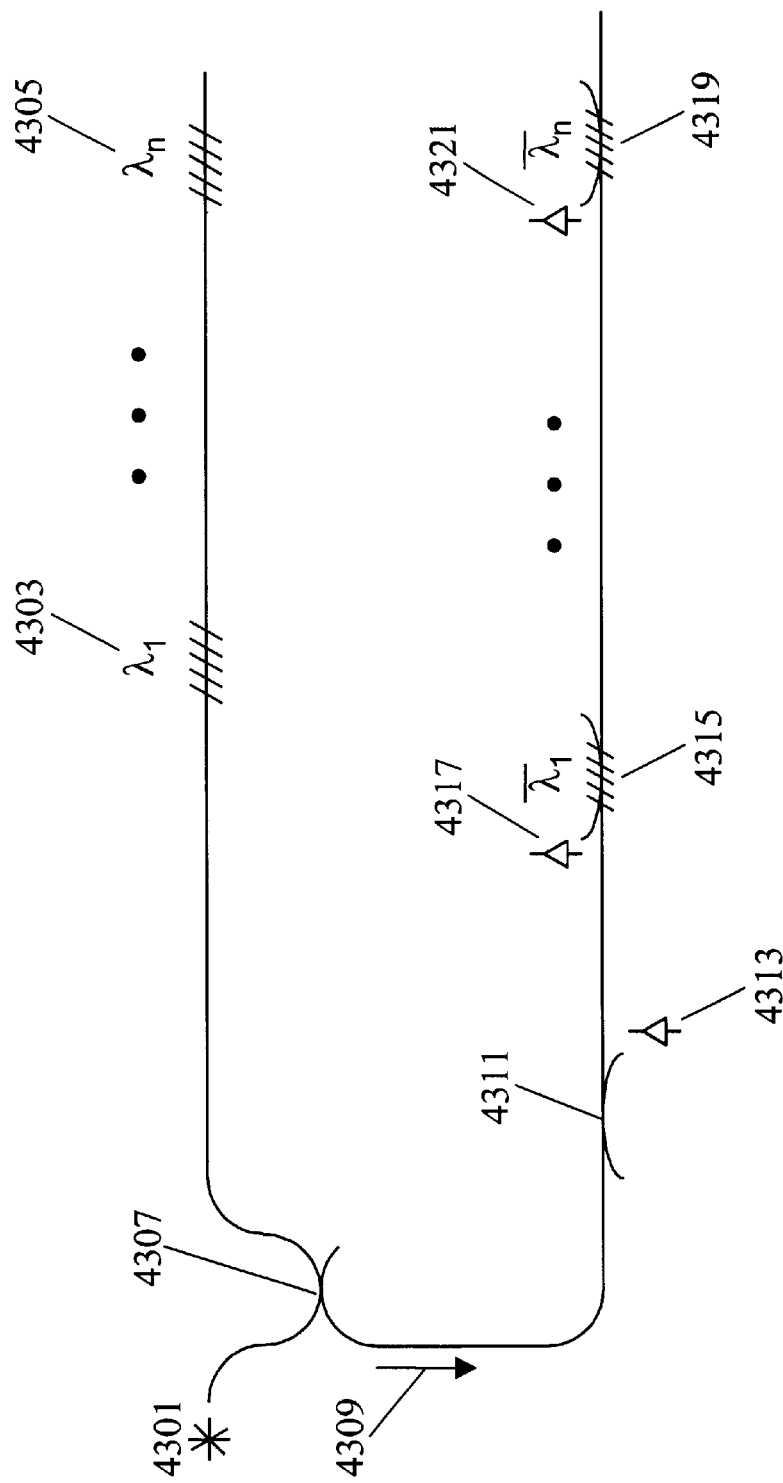
FIG. 55 is a diagram showing how gratings written into beam splatters can be employed to efficiently multiplex a high speed fiber grating demodulation system.

FIG. 55 shows a system that also is a single fiber output configuration. In this case the light source 4301 may be a broadband light source or a tunable laser diode. When the light source is a broadband light source that illuminates a series of fiber grating sensors 4303 . . . 4305 simultaneously, the light reflected off the fiber gratings 4303 and 4305 is split by the coupler 4307 into the light beam 4309. A tap coupler 4311 is used to couple a small amount of light to the reference detector 4313 that monitors system level light fluctuations. A combination fiber grating filter/beamsplitter 4315 is used to modulate light reflected from the fiber grating sensor 4303 onto the output detector 4317. A combination fiber grating filter/beamsplitter 4319 is used modulate light reflected from the fiber grating sensor 4305 onto the output detector 4321. By taking the ratio of the outputs of detectors 4317 and 4313 the spectral fluctuations of fiber grating sensor 4303, which is centered about $\lambda_1$, can be tracked and environmental changes measured. Similarly by taking the ratio of the outputs of detectors 4321 and 4313 the spectral fluctuations of the fiber grating sensor 4305 which is centered about $\lambda_n$ can be tracked and environmental changes measured.

Many changes, modifications, alterations and other uses and applications which do not depart from the spirit and scope of the invention are deemed to be covered by the invention which is limited only by the claims which follow.

What is claimed is:

1. An environmental sensor to measure moisture or chemical content, said sensor including:
   (a) a fiber grating positioned between plates, and,
   (b) a layer of material that expands and contracts with moisture or chemical content, and,
   (c) a clamp surrounding the plates so that transverse force is applied to the fiber grating as the layer of material expands or contracts with moisture or chemical content.

2. An environmental sensor as in claim 1 further including:
   (a) multiple stacks of plates and layers of material that expand and contract with moisture or chemical content to exert transverse force on the fiber grating.

3. An environmental sensor as in claim 1 further including:
   (a) one of the plates having a V groove to position the optical fiber.

4. An environmental sensor as in claim 3 further including:
   (a) guides to position the plates for optimum transverse loading of the optical fiber grating.

5. An environmental sensor as in claim 3 further including:
   (a) a second fiber grating positioned in a second V groove plate opposite said first fiber grating and V groove plate, and,
   (b) centered dual separated plates with a layer of moisture/chemically responsive material between.

6. An environmental sensor as recited in claim 1 further including:
   (a) an optical fiber without a fiber grating, positioned in substantially the same orientation as the optical fiber containing the fiber grating, and
   (b) a dual parallel V groove plate in which the optical fiber with the fiber grating and the optical fiber without a fiber grating are positioned.

7. An environmental sensor as recited in claim 1 further including:

(a) plates with a beveled edge containing the layer of material that expands or contracts with the presence of moisture or chemical content.

8. An environmental sensor as recited in claim 1 further including:
   (a) plates that are permeable to moisture or chemical content.

9. An environmental sensor as recited in claim 1 further including:
   (a) a triple V groove for one plate with the two outer grooves containing fibers without fiber gratings and the center fiber containing a fiber grating.

10. An environmental sensor as recited in claim 1 further including:
    (a) the layer of material that expands or contracts being placed substantially on the fiber containing the fiber grating.

11. An environmental sensor as recited in claim 1 further comprising:
    (a) composite material placed around the fiber grating to orient it.

12. An environment sensor as recited in claim 11 further including:
    (a) a layer of material that expands or contracts with moisture or chemical content between the two plates that exert transverse force.

13. An environmental fiber grating strain sensor including:
    (a) birefringent optical fiber with a fiber grating written into it, and,
    (b) a coating surrounding said fiber, and
    (c) flats impressed on the coating to indicate orientation of the birefringent axes.

14. An environmental fiber grating strain sensor as recited in claim 13, further including:
    (a) a plurality of fiber gratings.

15. An environmental fiber grating strain sensor as recited in claim 13, further including:
    (a) said coating being moisture/chemical content responsive.

* * * * *